(12) United States Patent
Zhang et al.

(10) Patent No.: US 10,349,484 B1
(45) Date of Patent: Jul. 9, 2019

(54) SOLID STATE LIGHTING DEVICES WITH REDUCED MELATONIN SUPPRESSION CHARACTERISTICS

(71) Applicant: Cree, Inc., Durham, NC (US)

(72) Inventors: Fan Zhang, Goleta, CA (US); Ryan Gresback, Santa Barbara, CA (US); Antony Paul van de Ven, Hong Kong (HK); Robert Glass, Chapel Hill, NC (US); Bernd P. Keller, Santa Barbara, CA (US)

(73) Assignee: CREE, INC., Durham, NC (US)

( * ) Notice: Subject to any disclaimer, the term of this patent is extended or adjusted under 35 U.S.C. 154(b) by 0 days.

(21) Appl. No.: 15/994,483

(22) Filed: May 31, 2018

(51) Int. Cl.
| | |
|---|---|
| H05B 33/08 | (2006.01) |
| H01L 33/08 | (2010.01) |
| H01L 33/26 | (2010.01) |
| A61N 5/06 | (2006.01) |
| A61M 21/02 | (2006.01) |
| H01L 33/50 | (2010.01) |
| A61M 21/00 | (2006.01) |

(52) U.S. Cl.
CPC ......... *H05B 33/0857* (2013.01); *A61M 21/02* (2013.01); *A61N 5/0618* (2013.01); *H01L 33/08* (2013.01); *H01L 33/26* (2013.01); *H01L 33/502* (2013.01); *A61M 2021/0083* (2013.01); *A61N 2005/0652* (2013.01)

(58) Field of Classification Search
CPC ... H05B 33/0857; H01L 33/502; H01L 33/08; H01L 51/52
See application file for complete search history.

(56) References Cited

U.S. PATENT DOCUMENTS

| | | | |
|---|---|---|---|
| 6,600,175 B1 | 7/2003 | Baretz et al. | |
| 8,018,135 B2 | 9/2011 | Van De Ven et al. | |
| 8,814,621 B2 | 8/2014 | Seibel, II | |
| 9,159,888 B2 | 10/2015 | Chitnis et al. | |
| 10,022,556 B1 * | 7/2018 | Holbert | A61N 5/0618 |
| 2017/0133357 A1 * | 5/2017 | Kuo | H01L 25/167 |
| 2018/0052275 A1 * | 2/2018 | Lee | H01L 33/507 |
| 2018/0130928 A1 * | 5/2018 | Vick | H01L 33/504 |
| 2018/0139817 A1 * | 5/2018 | Yamakawa | F21S 2/00 |

OTHER PUBLICATIONS

"Can I Get LED Luminaires with LEDs That Look Like HPS?" Access Fixtures: High-Performance Lighting Solutions, Available online at: <<https://www.accessfixtures.com/leds-that-look-like-hps/>>, Accessed Jul. 30, 2018, 6 pages.
Al Enezi, J., et al., "A 'Melanopid' Spectral Efficiency Function Predicts the Sensitivity of Melanopsin Photoreceptors to Polychromatic Lights," Journal of Biological Rhythms, vol. 26, Issue 4, Jul. 19, 2011, pp. 314-323.
Cree, Inc., "Cree® XLamp® MHB-B LEDs," Cree Product Family Data Sheet: CLD-DS146 Rev 1E, Cree, Inc., Available online at: <<http://www.cree.com/led-components/media/documents/ds-MHBB.pdf>>, 2016-2017, 25 pages.
Cree, Inc., "Cree® XLamp® XT-E LEDs," Cree Product Family Data Sheet: CLD-DS41 Rev 16C, Cree, Inc., Available online at: <<http://www.cree.com/led-components/media/documents/XLampXTE.pdf>>, 2011-2018, 44 pages.
Cree, Inc., "Cree® XLamp® XP-G3 LEDs," Cree Product Family Data Sheet: CLD-DS139 Rev 1F, Cree, Inc., Available online at: <<http://www.cree.com/led-components/media/documents/dsXPG3.pdf>>, 2016-2018, 37 pages.
Cree, Inc., "Cree® XLamp® XP-L2 LEDs," Cree Product Family Data Sheet: CLD-DS149 Rev 0D, Cree, Inc., Available online at: <<http://www.cree.com/led-components/media/documents/dsxpl2.pdf>>, 2016-2017, 25 pages.
Cree, Inc., "RSW Series: RSW™ LED Street Luminaire—Medium," Cree Product Specification Sheet, Version 3, Cree Inc., Available online at: <<http://api.icentera.com/v2/getfile.aspx?f=571981BD289D50AAD8340CB2D3DA1025B66F9D512439877E5C2FF61752A68BE787126CEAA8424A4B>>, Last revised Dec. 22, 2017, 6 pages.
Cree, Inc., "XSP Series: XSP1™ LED Street/Area Light—Single Module—Version B," Cree Product Specification Sheet, Version 6, Cree, Inc., Available online at: <<http://api.icentera.com/v2/getfile.aspx?f=904BA32F0E4F06F14B599412D4BC913020799393494A6959E586082BA18E266A46C660236C87C980>>, Last revised Oct. 19, 2017, 6 pages.
Cree, Inc., "LEDway® Series: LEDway® LED Street Light," Cree Product Specification Sheet, Version 4, Cree, Inc., Available online at: <<http://api.icentera.com/v2/getfile.aspx?f=904BA32F0E4F06F14B599412D4BC913020799393494A6959E586082BA18E266A98927A105457C222>, Last revised Feb. 2, 2018, 8 pages.
Cree, Inc., "RUL Series: RUL™ LED Rural Utility Luminaire," Cree Product Specification Sheet, Version 10, Cree, Inc., Available online at: <<http://api.icentera.com/v2/getfile.aspx?f=904BA32F0E4F06F14B599412D4BC913020799393494A6959E586082BA18E266AFB3E226CA01114A9>, Last revised May 8, 2017, 4 pages.
Falchi, F., et al., "Limiting the impact of light pollution on human health, environment and stellar visibility," Journal of Environmental Economics and Management, vol. 92, Issue 10, Available online Jul. 13, 2011, pp. 2714-2722.

(Continued)

*Primary Examiner* — Donald L Raleigh
(74) *Attorney, Agent, or Firm* — Withrow & Terranova, P.L.L.C.; Vincent K. Gustafson

(57) ABSTRACT

Solid state lighting devices with melatonin suppression characteristics that ameliorate or reduce symptoms of circadian rhythm disorders or other health conditions. Aspects disclosed herein additionally relate to providing one or more of the foregoing effects while maintaining color rendering index (CRI) values acceptably high for the intended use, as well as providing lighting devices with high luminous efficacy and enhanced energy efficiency. A solid state lighting device includes one or more solid state emitters and one or more lumiphoric materials that provide aggregated emissions of the solid state lighting device. The aggregated emissions have a warm correlated color temperature (CCT) with a color point that is off of the blackbody locus (BBL) by a certain distance.

23 Claims, 19 Drawing Sheets

(56) References Cited

OTHER PUBLICATIONS

Ignialight, "Amber White LED—Color Temperature 2200K," Ignialight—Manufacturers of luminaires with LED technology, Available online at: <<https://www.ignialight.com/en/news/detail/id/100/amber-white-led-color-temperature-2200k>>, Accessed Jul. 20, 2018, 2 pages.

Kraus, L. J., et al., "Human and Environmental Effects of Light Emitting Diode (LED) Community Lighting," Report of the Council on Science and Public Health, CSAPH Report 2-A-16, Action of the AMA House of Delegates 2016 Annual Meeting, Available online at: <<https://www.ama-assn.org/sites/default/files/media-browser/public/about-ama/councils/Council%20Reports/council-on-science-public-health/a16-csaph2.pdf>>, 2016, 9 pages.

Lucas, R. J., et al., "Measuring and using light in the melanopsin age," Trends in Neuroscience, vol. 37, No. 1, Jan. 2014, pp. 1-9.

Rea, M. S., et al., "Circadian light," Journal of Circadian Rhythms, vol. 8, No. 2, Feb. 13, 2010, pp. 1-10.

Rea, M. S., et al., "Light as a circadian stimulus for architectural lighting," Lighting Research & Technology, vol. 50, Issue 4, Dec. 6, 2016, pp. 497-510.

\* cited by examiner

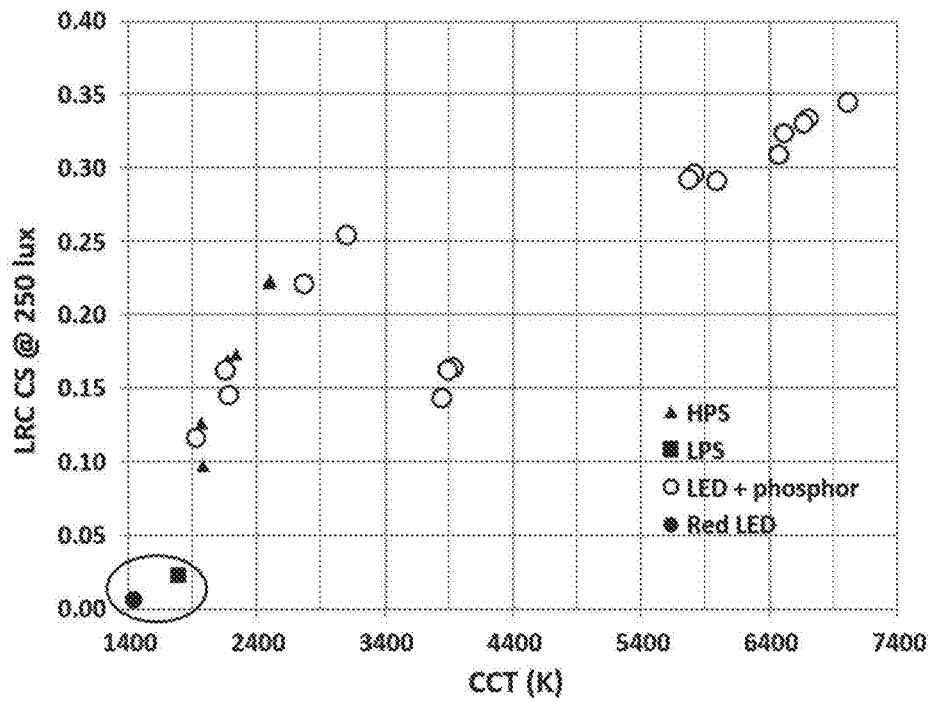
*FIG._5A*
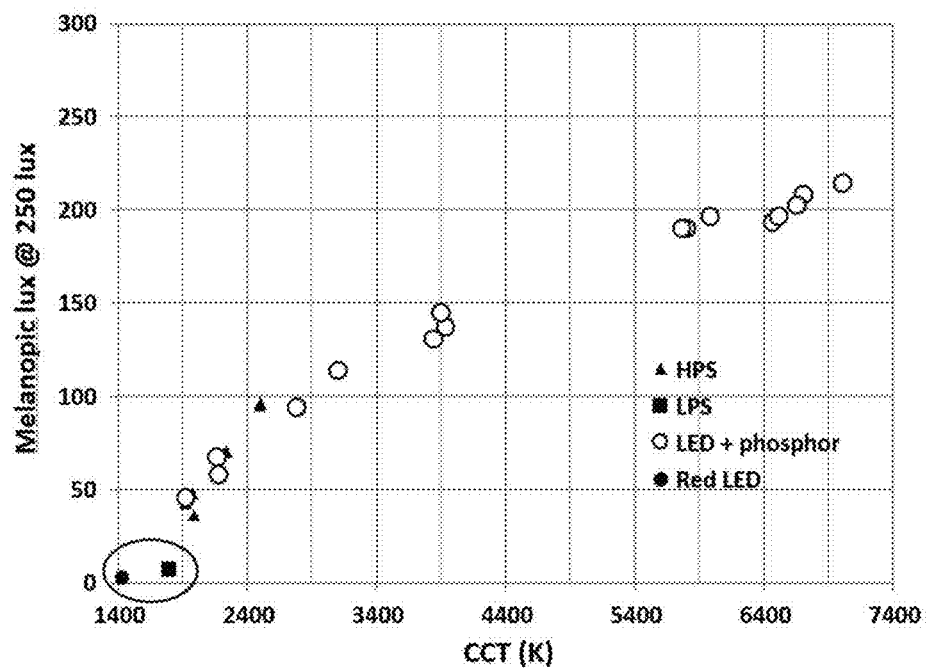
*FIG._5B*

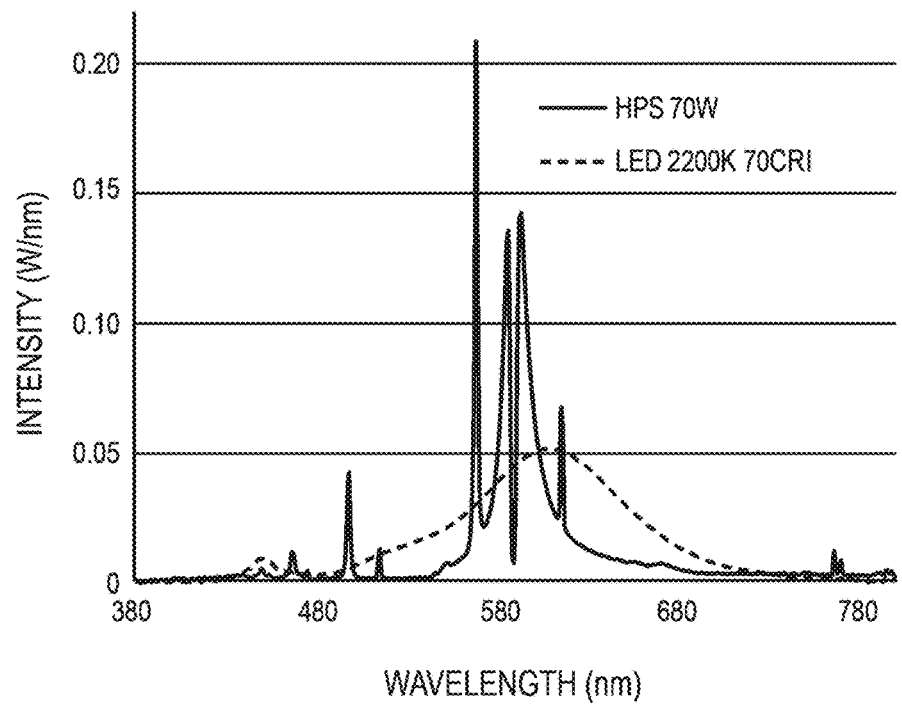
FIG._6B
| Booth | LED 2200K 70CRI | HPS 70W |
|---|---|---|
| Spectral mix | Blue LED + Y/G + R | NA |
| CCT: | 2153 | 1981 |
| Duv: | 0.0019 | 0.0039 |
| CRI Ra: | 73 | 9 |
| R9: | -23 | -264 |
| LER: | 334 | 414 |
| MPB% | 66% | 54% |
| CLA@250lx | 121.0 | 67.5 |
| Melanopic lux@250lx | 67.6 | 35.9 |
FIG._6C

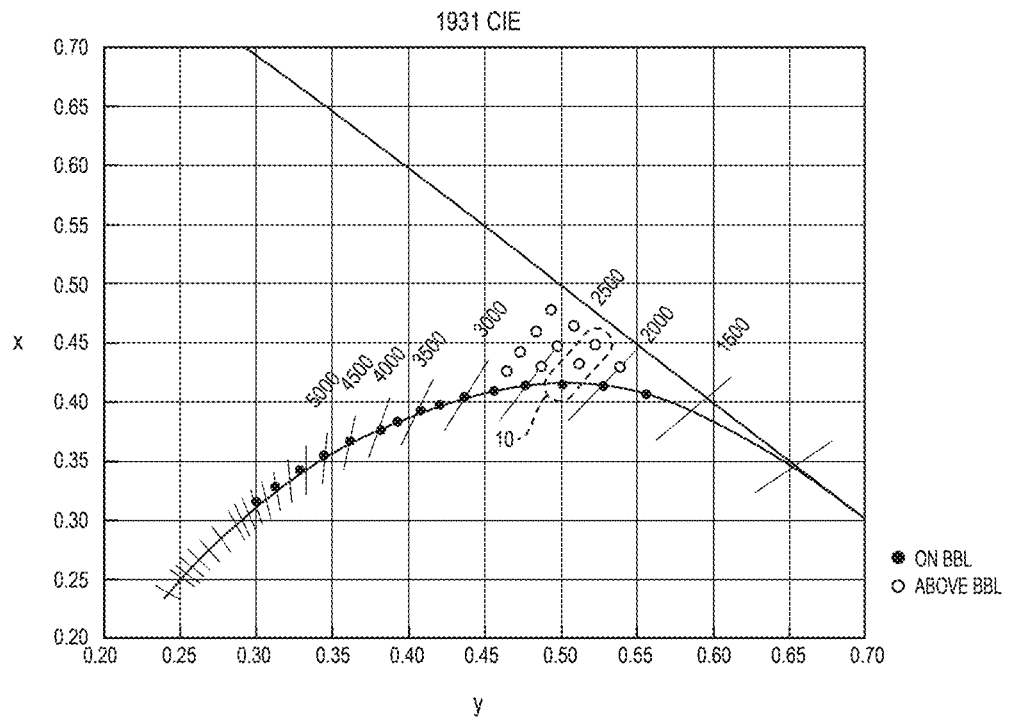
FIG._7A
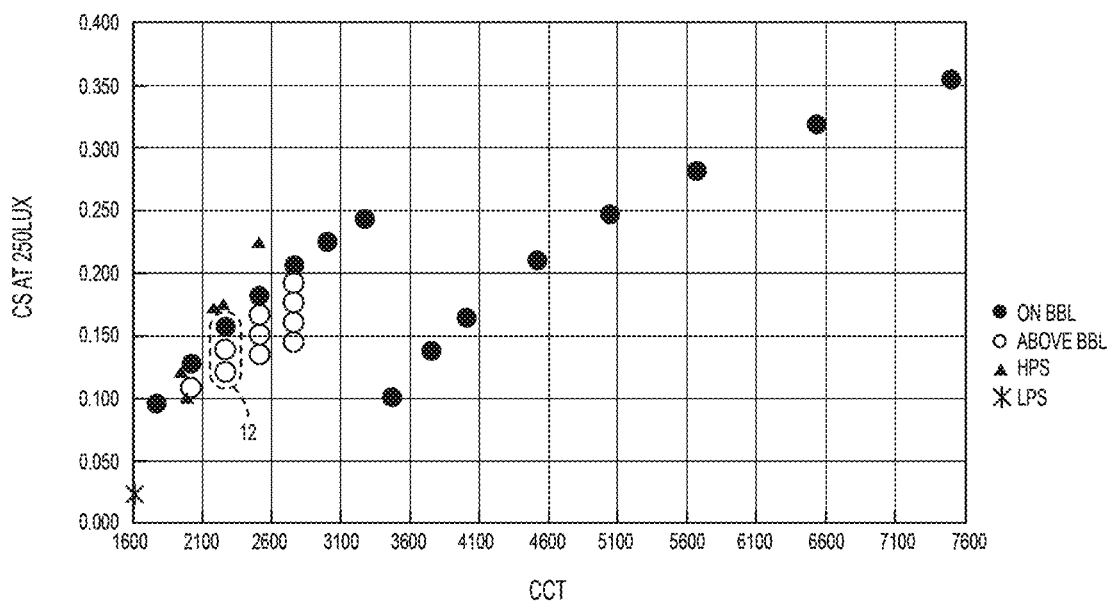
FIG._7B

| LED + Phosphor | CCT | Duv | LER | CS @ 250lx | CRI | Rf TM530 | Rg TM530 | Rg' | Lx | Qg | Phos1 | Phos1 thick | Phos2 | Phos2 thick | Phos3 | Phos3 thick | Excite pk nm | Excite cx | Excite cy | Output ccx | Output ccy | LPW (est.) | CLA @ 250 lx | Amelv |
|---|---|---|---|---|---|---|---|---|---|---|---|---|---|---|---|---|---|---|---|---|---|---|---|---|
| Blue LED + YAG/Red | 2750 | 0.0000 | 304 | 0.096 | 64 | 56 | 94 | -41 | 250 | 92 | red | 2.82 | Yellow/green | 0.18 | Yellow/green | 2.44 | 440 | 0.160 | 0.016 | 0.555 | 0.436 | 102 | 67.0 | 0.11 |
| Blue LED + YAG/Red | 2000 | 0.0000 | 319 | 0.138 | 69 | 61 | 98 | -29 | 250 | 95 | red | 3.94 | Yellow/green | 0.18 | Yellow/green | 2.64 | 440 | 0.160 | 0.016 | 0.527 | 0.413 | 108 | 91.8 | 0.17 |
| Blue LED + YAG/Red | 2000 | 0.0050 | 329 | 0.106 | 68 | 67 | 87 | -35 | 250 | 73 | red | 2.14 | Yellow/green | 0.18 | Yellow/green | 3.53 | 440 | 0.160 | 0.016 | 0.539 | 0.429 | 111 | 76.2 | 0.14 |
| Blue LED + YAG/Red | 2250 | 0.0000 | 329 | 0.158 | 72 | 63 | 100 | -22 | 250 | 96 | red | 3.50 | Yellow/green | 0.17 | Yellow/green | 2.73 | 440 | 0.160 | 0.016 | 0.503 | 0.413 | 114 | 116.0 | 0.21 |
| Blue LED + YAG/Red | 2250 | 0.0050 | 339 | 0.140 | 70 | 67 | 94 | -27 | 250 | 84 | red | 1.58 | Yellow/green | 0.17 | Yellow/green | 3.32 | 440 | 0.160 | 0.016 | 0.511 | 0.431 | 116 | 101.3 | 0.19 |
| Blue LED + YAG/Red | 2250 | 0.0100 | 351 | 0.121 | 68 | 70 | 80 | -34 | 250 | 61 | red | 1.73 | Yellow/green | 0.18 | Yellow/green | 4.54 | 440 | 0.160 | 0.016 | 0.523 | 0.448 | 119 | 85.7 | 0.16 |
| Blue LED + YAG/Red | 2500 | 0.0000 | 335 | 0.183 | 73 | 64 | 100 | -17 | 250 | 97 | red | 1.18 | Yellow/green | 0.16 | Yellow/green | 2.72 | 440 | 0.160 | 0.016 | 0.477 | 0.414 | 118 | 139.4 | 0.25 |
| Blue LED + YAG/Red | 2500 | 0.0050 | 345 | 0.166 | 71 | 67 | 96 | -22 | 250 | 90 | red | 1.22 | Yellow/green | 0.17 | Yellow/green | 3.18 | 440 | 0.160 | 0.016 | 0.487 | 0.430 | 120 | 125.1 | 0.23 |
| Blue LED + YAG/Red | 2500 | 0.0100 | 356 | 0.152 | 70 | 70 | 90 | -28 | 250 | 78 | red | 1.28 | Yellow/green | 0.17 | Yellow/green | 3.90 | 440 | 0.160 | 0.016 | 0.497 | 0.447 | 123 | 110.9 | 0.21 |
| Blue LED + YAG/Red | 2500 | 0.0150 | 369 | 0.133 | 68 | 69 | 74 | -35 | 250 | 54 | red | 1.39 | Yellow/green | 0.17 | Yellow/green | 5.40 | 440 | 0.160 | 0.016 | 0.508 | 0.464 | 127 | 95.6 | 0.19 |
| Blue LED + YAG/Red | 2750 | 0.0000 | 339 | 0.206 | 73 | 65 | 100 | -14 | 250 | 98 | red | 0.94 | Yellow/green | 0.18 | Yellow/green | 2.69 | 440 | 0.160 | 0.016 | 0.456 | 0.410 | 121 | 160.9 | 0.28 |
| Blue LED + YAG/Red | 2750 | 0.0050 | 349 | 0.192 | 72 | 67 | 97 | -19 | 250 | 92 | red | 0.96 | Yellow/green | 0.18 | Yellow/green | 3.06 | 440 | 0.160 | 0.016 | 0.464 | 0.425 | 124 | 147.5 | 0.27 |
| Blue LED + YAG/Red | 2750 | 0.0100 | 360 | 0.178 | 70 | 69 | 93 | -25 | 250 | 85 | red | 0.98 | Yellow/green | 0.18 | Yellow/green | 3.56 | 440 | 0.160 | 0.016 | 0.473 | 0.442 | 127 | 134.2 | 0.25 |
| Blue LED + YAG/Red | 2750 | 0.0150 | 372 | 0.163 | 69 | 72 | 87 | -31 | 250 | 73 | red | 1.02 | Yellow/green | 0.19 | Yellow/green | 4.35 | 440 | 0.160 | 0.016 | 0.483 | 0.460 | 130 | 120.7 | 0.23 |
| Blue LED + YAG/Red | 2750 | 0.0200 | 385 | 0.146 | 67 | 68 | 71 | -40 | 250 | 51 | red | 1.08 | Yellow/green | 0.19 | Yellow/green | 6.02 | 440 | 0.160 | 0.016 | 0.493 | 0.478 | 133 | 106.0 | 0.21 |

FIG. 7C

SOLID STATE LIGHTING DEVICES WITH REDUCED MELATONIN SUPPRESSION CHARACTERISTICS

FIELD OF THE DISCLOSURE

The present disclosure relates to solid state lighting devices, including devices with lumiphors arranged to be stimulated by electrically activated solid state emitters, and relates to associated methods of making and using such devices.

BACKGROUND

Solid state lighting devices such as light-emitting diodes (LEDs) are increasingly used in both consumer and commercial applications. Advancements in LED technology have resulted in highly efficient and mechanically robust light sources with a long service life. Accordingly, modern LEDs have enabled a variety of new display applications and are increasingly utilized for general illumination applications, often replacing incandescent and fluorescent light sources.

LEDs are solid state devices that convert electrical energy to light and generally include one or more active layers of semiconductor material (or an active region) arranged between oppositely doped n-type and p-type layers. When a bias is applied across the doped layers, holes and electrons are injected into the one or more active layers where they recombine to generate emissions such as visible light or ultraviolet (UV) emissions or infrared (IR) emissions. A LED chip typically includes an active region that may be fabricated, for example, from silicon carbide, gallium nitride, gallium phosphide, aluminum nitride, gallium arsenide-based materials, and/or from organic semiconductor materials.

Solid state emitters may include lumiphoric materials (also known as lumiphors) that absorb a portion of emissions having a first peak wavelength emitted by the emitter and re-emit light having a second peak wavelength that differs from the first peak wavelength. Phosphors, scintillators, and lumiphoric inks are common lumiphoric materials. Light perceived as white or near-white may be generated by a combination of red, green, and blue (RGB) emitters, or, alternatively, by combined emissions of a blue LED and a lumiphor such as a yellow phosphor (e.g., YAG:Ce or Ce:YAG). In the latter case, a portion of the blue LED emissions pass through the phosphor, while another portion of the blue emissions is downconverted to yellow, and the blue and yellow light in combination are perceived as white. White light may also be produced by stimulating phosphors or dyes of multiple colors with a violet or UV LED source.

Emissions of a blue LED in combination with a yellow or green lumiphoric material may be near-white in character and referred to as "blue-shifted yellow" ("BSY") light or "blue-shifted green" ("BSG") light. Addition of red (or red-orange) spectral output from a red-emitting LED (to yield a "BSY+R" device) or from a red lumiphoric material (to yield a "BS(Y+R)" device) may be used to increase the warmth of the aggregated light output and better approximate light produced by incandescent lamps.

Color reproduction is commonly measured using color rendering index (CRI) or average color rendering index (CRI Ra). To calculate the CRI, the color appearance of 14 reflective samples is simulated when illuminated by a reference radiator (illuminant) and the test source. The CRI Ra is a modified average utilizing the first eight indices, all of which have low to moderate chromatic saturation. (R9 is one of six saturated test colors not used in calculating CRI, with R9 embodying a large red content.) The CRI and CRI Ra are used to determine how closely an artificial light source matches the color rendering of a natural light source at the same correlated color temperature (CCT). Daylight has a high CRI Ra (approximately 100), with incandescent bulbs also being relatively close (CRI Ra greater than 95), and fluorescent lighting being less accurate (with typical CRI Ra values of approximately 70-80).

The reference spectra used in color rendering index calculations were chosen as ideal illumination sources defined in terms of their color temperature. As a heated object becomes incandescent, it first glows reddish, then yellowish, then white, and finally bluish. Thus, apparent colors of incandescing materials are directly related to their actual temperature (in Kelvin (K)). Practical materials that incandesce are said to have CCT values that are directly related to color temperatures of blackbody sources.

Aspects relating to the inventive subject matter disclosed herein may be better understood with reference to the 1931 CIE (Commission International de l'Eclairage) Chromaticity Diagram, which is well-known and of which a copy is reproduced in FIG. 1. The 1931 CIE Chromaticity Diagram maps out the human color perception in terms of two CIE parameters x and y. The spectral colors are distributed around the edge of the outlined space, which includes all of the hues perceived by the human eye. The boundary line represents maximum saturation for the spectral colors. The chromaticity coordinates (i.e., color points) that lie along the blackbody locus (BBL) (also known as the Planckian locus) obey Planck's equation: $E(\lambda)=A\lambda^{-5}/(e^{B/T}-1)$, where E is the emission intensity, $\lambda$ is the emission wavelength, T is the color temperature of the blackbody, and A and B are constants. Color coordinates that lie on or near the BBL (which embodies a curved line emanating from the right lower corner) yield pleasing white light to a human observer. The 1931 CIE Diagram includes temperature listings along the BBL, with these temperature listings showing the color path of a blackbody radiator that is caused to increase to such temperatures. As a heated object becomes incandescent, it first glows reddish, then yellowish, then white, and finally bluish. This occurs because the wavelength associated with the peak radiation of the blackbody radiator becomes progressively shorter with increased temperature, consistent with the Wien Displacement Law. Illuminants which produce light that is on or near the BBL can thus be described in terms of their color temperature. The white area proximate to (i.e., within approximately a MacAdam eight-step ellipse of) of the BBL and between 2,500 K and 10,000 K, is shown in FIG. 1.

The term "white light" or "whiteness" does not clearly cover the full range of colors along the BBL since it is apparent that a candle flame and other incandescent sources appear yellowish, i.e., not completely white. Accordingly, the color of illumination may be better defined in terms of CCT and in terms of its proximity to the BBL. The pleasantness and quality of white illumination decreases rapidly if the chromaticity point of the illumination source deviates from the BBL by a distance of greater than 0.01 in the x, y chromaticity system. This corresponds to the distance of about a MacAdam four-step ellipse, a standard employed by the lighting industry. A lighting device emitting light having color coordinates that are within a MacAdam four-step ellipse of the BBL and that has a CRI Ra greater than 80 is generally acceptable as a white light for general illumination purposes. A lighting device emitting light having color coordinates within a MacAdam seven- or eight-step ellipse of the BBL and that has a CRI Ra greater than 70 is used as the minimum standards for many other white lighting devices including compact fluorescent and solid state lighting devices. FIG. 2 illustrates MacAdam 2-step, 4-step, and 7-step ellipses for a CCT of 3200 K relative to a segment of the BBL (e.g., extending generally between 2900 K and 3500 K).

Quality artificial lighting generally attempts to emulate the characteristics of natural light. Natural light sources include daylight with a relatively high color temperature (e.g., ~5000 K) and incandescent lamps with a lower color temperature (e.g., ~2800 K). General illumination generally has a color temperature between 2,000 K and 10,000 K, with the majority of lighting devices for general illumination being between 2,700 K and 6,500 K. The white area proximate to (i.e., within approximately a MacAdam eight-step ellipse of) of the BBL and between 2,500 K and 10,000 K, is shown in FIG. 1.

The 1976 CIE Chromaticity Diagram, also well-known and readily available to those of ordinary skill in the art, maps human color perception in terms of CIE parameters u' and v'. The 1976 CIE Chromaticity Diagram (also known as the (u'v') chromaticity diagram) is reproduced at FIG. 3. The spectral colors are distributed around the edge of the outlined space, which includes all of the hues perceived by the human eye. The boundary line represents maximum saturation for the spectral colors. The 1976 CIE Chromaticity Diagram is similar to the 1931 Diagram, except that the 1976 Diagram has been modified such that similar distances on the Diagram represent similar perceived differences in color. Since similar distances on the 1976 Diagram represent similar perceived differences in color, deviation from a point on the 1976 Diagram can be expressed in terms of the coordinates, u' and v', e.g., distance from the point=$(\Delta u'^2 + \Delta v'^2)^{1/2}$, and the hues defined by a locus of points that are each a common distance from a specified hue consist of hues that would each be perceived as differing from the specified hue to a common extent. Duv is a metric that quantifies the distance between a color point and a point on the BBL having the same CCT in the u', v' coordinate system. A negative Duv value indicates a color point below the BBL and a positive Duv value indicates a point above the BBL.

Luminous efficacy is a measure of how well a light source produces visible light, and represents the ratio of luminous flux to power (with the power being either radiant flux or total power consumed by a source, depending on the context). Wavelengths of light outside of the visible spectrum are not useful for illumination because they cannot be seen by the human eye. Moreover, the human eye exhibits greater response to some wavelengths of light than to others, even within the visible spectrum. Response of the human eye to light also varies with respect to the level of intensity of light.

It has been recently recognized that photosensitive retinal ganglion cells expressing the photopigment melanopsin is involved not only in circadian photoentrainment, but also in perceived brightness of light. Melanopsin photoreceptors are sensitive to a range of wavelengths and reach peak light absorption at blue light wavelengths around 480 nm. A "melanopic" spectral efficiency function has been determined to predict the sensitivity of melanopsin photoreceptors to polychromatic lights. FIG. 4 is a plot of a melanopic spectral efficiency function, expressed in (p) versus wavelength (nm), derived from experimentation performed on transgenic mice lacking rod and cone photoreception, and as described in al Enezi et al., "A 'Melanopic' Spectral Efficiency Function Predicts the Sensitivity of Melanopsin Photoreceptors to Polychromatic Lights," J. Biological Rhythms, Vol. 26, No. 4, August 2011, 314-323. The curve of FIG. 4 involves weighting of spectral irradiance profiles (for a range of colored and broad-spectrum white lights) as according to spectral sensitivity of a family of putative opsin photopigments with a maximum response wavelength in a range of 400 to 550 nm, with data being fit with a Gaussian distribution peaking at 484 nm.

In animals, circulating levels of the hormone melatonin (also known chemically as N-acetyl-5-methoxytryptamine) vary in a daily cycle, thereby allowing the entrainment of the circadian rhythms of several biological functions. Melatonin is produced in humans by the pineal gland, a small endocrine gland located in the center of the brain. The melatonin signal forms part of the system that regulates the sleep-wake cycle by chemically causing drowsiness and lowering the body temperature. Melatonin is commonly released in darkness (roughly 4-5 hours before sleep), and its production is suppressed by exposure to light. The light-dependent character of melatonin release and suppression aids in falling asleep and waking up. Nighttime light exposure can increase body temperature, and enhance alertness and performance.

Circadian rhythm disorders may be associated with changes in nocturnal activity (e.g., nighttime shift workers), changes in latitude or changes in longitude (e.g., jet lag), and/or seasonal changes in light duration (e.g., seasonal affective disorder, with symptoms including depression). It is principally blue light (e.g., including blue light at a peak wavelength value between 460 nm to 480 nm, with some activity from about 360 nm to about 600 nm), that suppresses melatonin and synchronizes the circadian clock, proportional to the light intensity and length of exposure. Exposure to principally blue light (e.g., emitted by artificial light sources generating emissions with significant blue content) at times when melatonin is typically released, such as nighttime, can detrimentally suppress melatonin production and disrupt the normal circadian rhythm.

The art continues to seek improved solid state lighting devices that provide desirable illumination characteristics and are capable of overcoming challenges associated with conventional lighting devices.

SUMMARY

Aspects disclosed herein relate to solid state lighting devices with melatonin suppression characteristics that ameliorate or reduce symptoms of circadian rhythm disorders or other health conditions in humans, as well as plants and animals. Aspects disclosed herein additionally relate to providing one or more of the foregoing effects while maintaining color rendering index (CRI) values acceptably high for the intended use, as well as providing lighting devices with high luminous efficacy and enhanced energy efficiency. Certain aspects disclosed herein relate to solid state lighting devices for outdoor lighting applications with reduced light pollution and lower impact on circadian rhythms while maintaining CRI values acceptably high for the intended use, as well as providing lighting devices with high luminous efficacy and enhanced energy efficiency.

In some aspects, the present disclosure relates to a solid state lighting device including at least one electrically activated solid state emitter configured to generate emissions having a peak wavelength in a range from 430 nanometers (nm) to 480 nm; a first lumiphoric material arranged to receive at least a portion of the emissions of the at least one electrically activated solid state emitter and responsively generate first lumiphor emissions having a peak wavelength in a range from 540 nm to 570 nm; and a second lumiphoric material arranged to receive at least a portion of the emissions of the at least one electrically activated solid state emitter and responsively generate second lumiphor emissions having a peak wavelength in a range from 605 nm to 650 nm. Aggregated emissions of the solid state lighting device include at least a portion of the emissions of each of the at least one electrically activated solid state emitter, the first lumiphor emissions, and the second lumiphor emissions; and the aggregated emissions have a correlated color temperature (CCT) in a range of from 1800 (Kelvin) K to 2600 K, and have a Duv of at least 0.005.

In some embodiments, the aggregated emissions have a CCT in a range of 1800 K to 2300K, or in a range of 2150 K to 2250K. In some embodiments, the aggregated emission have a Duv in a range from 0.005 to 0.020. In some embodiments, the aggregated emissions have a CRI of at least 65, or a CRI in a range of 65 to 85.

In some embodiments, the first lumiphoric material and the second lumiphoric material are dispersed together in a common binder. In other embodiments, the first lumiphoric material and the second lumiphoric material are arranged in discrete layers on the at least one electrically activated solid state emitter. In further embodiments, the second lumiphoric material is between the first lumiphoric material and the at least one electrically activated solid state emitter.

In some embodiments, the solid state lighting device includes a light-emitting diode (LED) package. In some embodiments, the solid state lighting device includes an outdoor lighting fixture or an indoor lighting fixture.

In some aspects, the present disclosure relates to a solid state lighting device including a first electrically activated solid state emitter; a first lumiphoric material arranged to receive at least a portion of emissions of the first electrically activated solid state emitter and responsively generate first lumiphor emissions; a second electrically activated solid state emitter; and a second lumiphoric material arranged to receive at least a portion of emissions of the second electrically activated solid state emitter and responsively generate second lumiphor emissions, wherein the second lumiphor emissions have a peak wavelength that differs from a peak wavelength of the first lumiphor emissions by at least 25 nm. Aggregated emissions of the solid state lighting device include at least a portion of the emissions of each of the first electrically activated solid state emitter, the second electrically activated solid state emitter, the first lumiphor emissions, and the second lumiphor emissions; and the aggregated emissions have a CCT in a range of from 1800 K to 2600 K, and have a Duv of at least 0.005.

In some embodiments, the first electrically activated solid state emitter is configured to generate emissions having a peak wavelength in a range from 430 nm to 480 nm and the first lumiphor emissions have a peak wavelength in a range from 540 nm to 570 nm. In some embodiments, the second electrically activated solid state emitter is configured to generate emissions having a peak wavelength in a range from 430 nm to 480 nm and the second lumiphor emissions have a peak wavelength in a range from 605 nm to 650 nm.

In some embodiments, the aggregated emissions have a CRI of at least 65, or a CRI in a range of 65 to 85.

In some aspects, the present disclosure relates to a solid state lighting device including a first electrically activated solid state emitter configured to generate emissions having a peak wavelength in a range from 430 nm to 480 nm; a first lumiphoric material arranged to receive at least a portion of the emissions of the first electrically activated solid state emitter and responsively generate first lumiphor emissions having a peak wavelength in a range from 540 nm to 570 nm; and a second electrically activated solid state emitter configured to generate emissions having a peak wavelength in a range from 605 nm to 650 nm. Aggregated emissions of the solid state lighting device include at least a portion of emissions of each of the first electrically activated solid state emitter, the first lumiphor emissions, and the second electrically activated solid state emitter; and the aggregated emissions have a CCT in a range of from 1800 K to 2600K, and have a Duv of at least 0.005.

In some embodiments, the solid state lighting device further includes a second lumiphoric material arranged to receive at least a portion of the emissions of the first electrically activated solid state emitter and responsively generate second lumiphor emissions having a peak wavelength in a range from 605 nm to 650 nm.

In some embodiments, the aggregated emissions have a CRI of at least 65, or a CRI in a range of 65 to 85.

In some aspects, embodiments disclosed herein include a solid state lighting device comprising: a first electrically activated solid state emitter; a first lumiphoric material arranged to receive at least a portion of emissions of the first electrically activated solid state emitter and responsively generate first lumiphor emissions; at least one other light emitter including at least one of the following items (a) or (b): (a) a second electrically activated solid state emitter, or (b) a second lumiphoric material arranged to receive at least a portion of emissions of the first electrically activated solid state emitter and responsively generate second lumiphor emissions; wherein aggregated emissions of the solid state lighting device include at least a portion of the emissions of each of the first electrically activated solid state emitter, the first lumiphoric material, and the at least one other light emitter; and wherein the aggregated emissions comprises at least one of the following features (i), (ii), or (iii): (i) a correlated color temperature (CCT) in a range of from 1950 K to 2050 K, a CRI of at least 70, and a circadian stimulus (CS) value of less than 0.125; or (ii) a correlated color temperature (CCT) in a range of from 2200 K to 2300 K, a CRI of at least 70, and a circadian stimulus (CS) value of less than 0.145; or (iii) a correlated color temperature (CCT) in a range of from 2450 K to 2550 K, a CRI of at least 70, and a circadian stimulus (CS) value of less than 0.17.

In some embodiments, the aggregated emissions have a Duv of at least 0.005.

In some embodiments, the solid state lighting device further comprises a luminaire efficiency rating (LER) of at least 335 when the aggregated emissions comprise a correlated color temperature (CCT) in a range of from 2200 K to 2300 K.

In some aspects, embodiments disclosed herein include a solid state lighting device comprising: a first electrically activated solid state emitter; a first lumiphoric material arranged to receive at least a portion of emissions of the first electrically activated solid state emitter and responsively generate first lumiphor emissions; at least one other light emitter including at least one of the following items (a) or (b): (a) a second electrically activated solid state emitter, or (b) a second lumiphoric material arranged to receive at least a portion of emissions of the first electrically activated solid state emitter and responsively generate second lumiphor emissions; wherein aggregated emissions of the solid state lighting device include at least a portion of the emissions of each of the first electrically activated solid state emitter, the first lumiphoric material, and the at least one other light emitter; and wherein the aggregated emissions comprises at least one of the following features (i), (ii), or (iii): (i) a correlated color temperature (CCT) in a range of from 1950 K to 2050 K, a CRI of at least 70, and a luminaire efficiency rating (LER) of at least 325; or (ii) a correlated color temperature (CCT) in a range of from 2200 K to 2300 K, a CRI of at least 70, and a luminaire efficiency rating (LER) of at least 335; or (iii) a correlated color temperature (CCT) in a range of from 2450 K to 2550 K, a CRI of at least 70, and a luminaire efficiency rating (LER) of at least 340.

In some embodiments, the aggregated emissions have a Duv of at least 0.005.

In some embodiments, the aggregated emissions comprises a correlated color temperature (CCT) in a range of from 2200 K to 2300 K, a CRI of at least 70, a luminaire efficiency rating (LER) of at least 335, and a circadian stimulus (CS) value of less than 0.145.

In some aspects, embodiments disclosed herein include a solid state lighting device comprising: a first electrically activated solid state emitter; a first lumiphoric material arranged to receive at least a portion of emissions of the first electrically activated solid state emitter and responsively generate first lumiphor emissions; at least one other light emitter including at least one of the following items (a) or (b): (a) a second electrically activated solid state emitter, or (b) a second lumiphoric material arranged to receive at least a portion of emissions of the first electrically activated solid state emitter and responsively generate second lumiphor emissions; wherein aggregated emissions of the solid state lighting device include at least a portion of the emissions of each of the first electrically activated solid state emitter, the first lumiphoric material, and the at least one other light emitter; and wherein the aggregated emissions have a circadian stimulus (CS) value of less than 0.17, and have a Duv of at least 0.005.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 5A is a plot of a circadian stimulus (CS) model versus CCT for various light sources including representative high-pressure sodium (HPS) and low-pressure sodium (LPS) light sources, a light-emitting diode (LED) with lumiphoric materials, and a red LED.

FIG. 5B is a plot of a melanopic lux model versus CCT for the same light sources plotted in FIG. 5A.

FIG. 6B provides spectral power distribution plots (in normalized intensity versus wavelength) for the two light sources of FIG. 6A.

FIG. 6C is a table listing various performance characteristics for the two light sources of FIG. 6A.

FIG. 7A provides a portion of a 1931 CIE diagram illustrating the relationship of various solid state lighting sources to the BBL.

FIG. 7B is a plot comparing CS values by CCT for each of the data points of FIG. 7A.

FIG. 7C is a table listing the various characteristics for each of the data points plotted in FIG. 7A and FIG. 7B.

DETAILED DESCRIPTION

Figure 1:
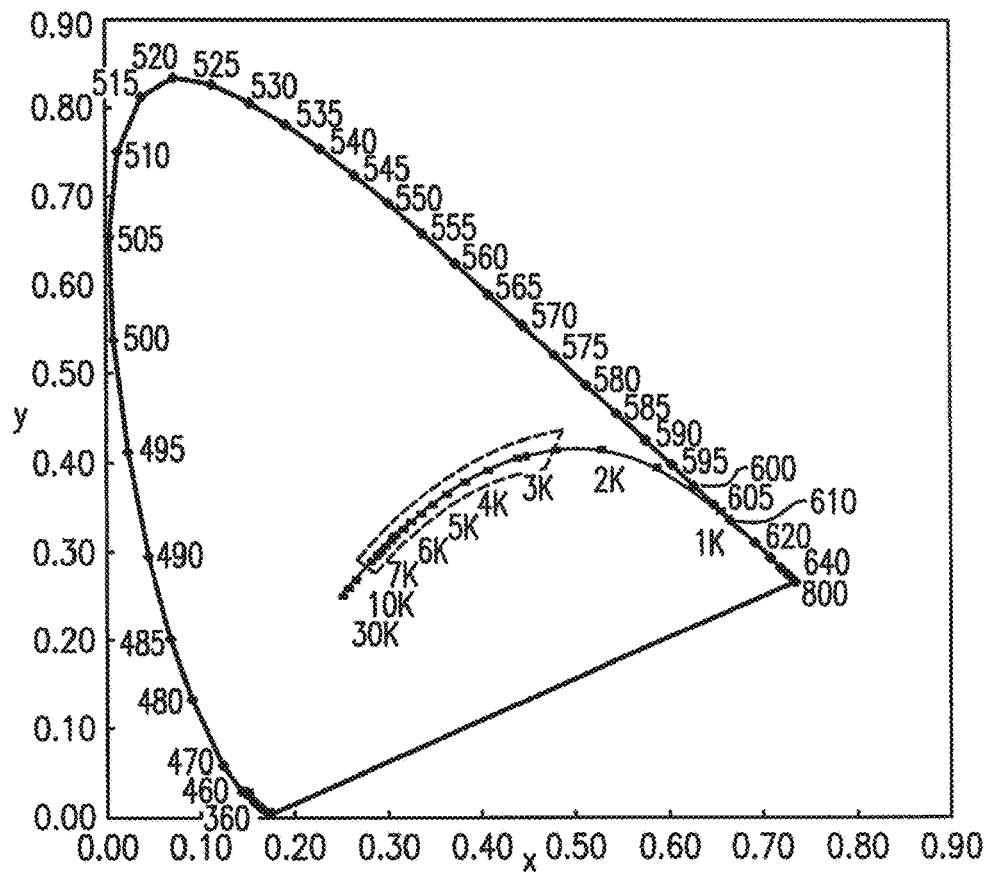
FIG. 1 is a 1931 CIE Chromaticity Diagram with identification of a white area proximate to (i.e., within approximately a MacAdam eight-step ellipse of) of the blackbody or Planckian locus (BBL), and identification of correlated color temperature (CCT) values ranging from 1,000 Kelvin (K) to 30,000 K.
Figure 2:
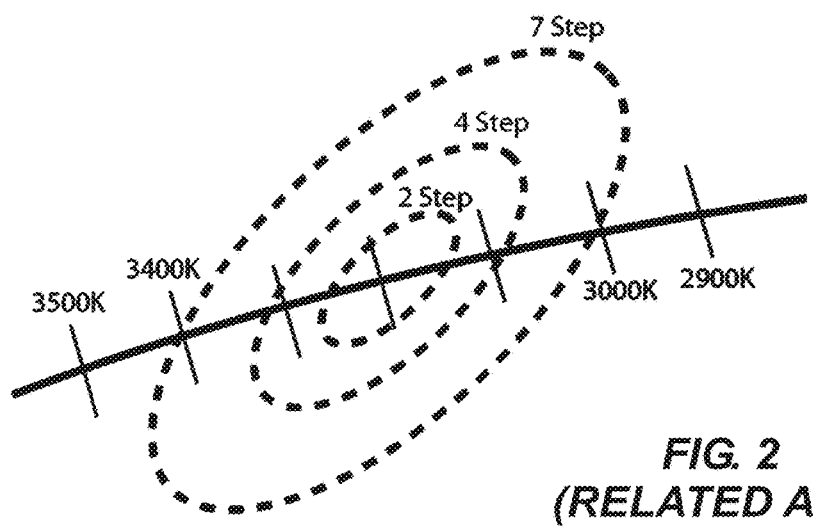
FIG. 2 illustrates MacAdam 2-step, 4-step, and 7-step ellipses for a CCT of 3200 K relative to a segment of the BBL.
Figure 3:
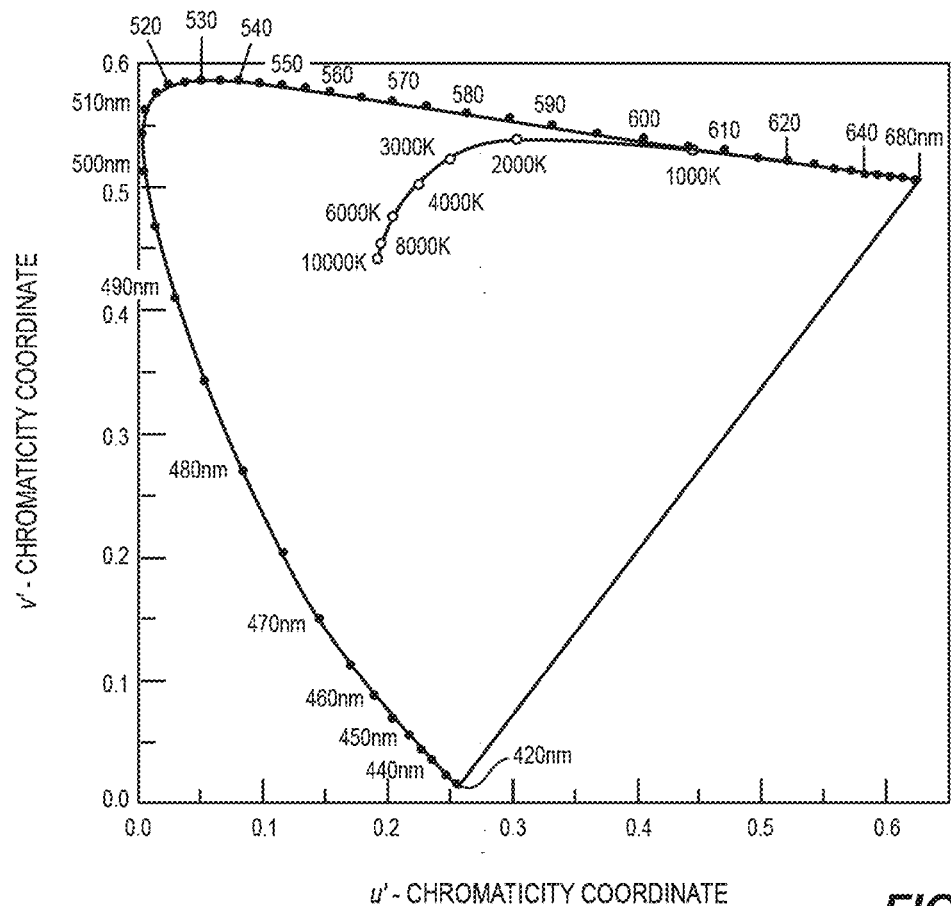
FIG. 3 is a 1976 CIE Chromaticity Diagram including identification of CCT values ranging from 1,000 K to 10,000 K.
Figure 4:
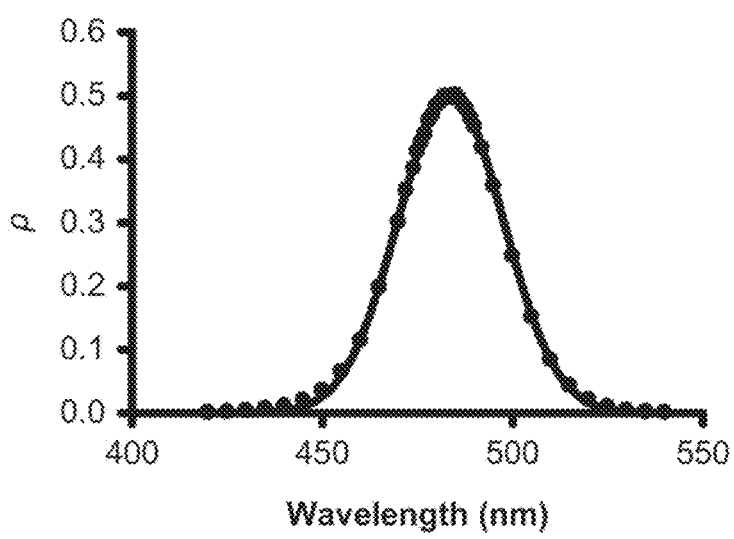
FIG. 4 provides a plot a melanopic spectral efficiency function, expressed in F test probability (p) versus wavelength, derived from experimentation performed on mice.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

The terms "solid state light emitter" or "solid state emitter" (which may be qualified as being "electrically activated") may include a light-emitting diode, laser diode, organic LED, and/or other semiconductor devices which include one or more semiconductor layers, which may include silicon, silicon carbide, gallium nitride and/or other semiconductor materials, a substrate which may include sapphire, silicon, silicon carbide and/or other microelectronic substrates, and one or more contact layers which may include metal and/or other conductive materials. Solid state light emitting devices according to embodiments disclosed herein may include, but are not limited to, III-V nitride based LED chips or laser chips fabricated on a silicon, silicon carbide, sapphire, or III-V nitride growth substrate, including (for example) devices manufactured and sold by Cree, Inc. of Durham, N.C.

Solid state light emitters may be used individually or in groups to emit one or more beams to stimulate emissions of one or more lumiphoric materials (e.g., phosphors, scintillators, lumiphoric inks, quantum dots, day glow tapes, etc.) to generate light at one or more peak wavelengths, or of at least one desired perceived color (including combinations of colors that may be perceived as white). Lumiphoric materials may be provided in the form of particles, films, or sheets. Quantum dot materials of various colors are commercially available from QD Vision, Inc. (Lexington, Mass., USA), Nanosys Inc. (Milpitas, Calif., USA), and Nanoco Technologies Ltd. (Manchester, United Kingdom), among others.

Inclusion of lumiphoric (also called "luminescent") materials in lighting devices as described herein may be accomplished by any suitable means, including: direct coating on solid state emitters; dispersal in encapsulant materials arranged to cover solid state emitters; coating on lumiphor support elements (e.g., by powder coating, inkjet printing, or the like); incorporation into diffusers or lenses; solid sheets or caps of lumiphoric material; and the like. Examples of lumiphoric materials are disclosed, for example, in U.S. Pat. Nos. 6,600,175, 8,018,135, and 8,814,621, and methods for coating light emitting elements with phosphors are disclosed in U.S. Pat. No. 9,159,888, with the foregoing patents being incorporated by reference herein. Other materials, such as light scattering elements (e.g., particles) and/or index matching materials, may be associated with a lumiphoric material-containing element or surface. One or more lumiphoric materials useable in devices as described herein may be down-converting or up-converting, or can include a combination of both types.

Examples of phosphors that may be used according to various embodiments include, without limitation, cerium (III)-doped yttrium aluminum garnet (Ce:YAG or YAG:Ce); yttrium aluminum oxide doped with cerium yttrium aluminum garnet (NYAG); green YAG (GNYAG), lutetium aluminum garnet (LuAG), green aluminate (GAL, including but not limited to GAL535); $(Sr,Ba,Ca)_{2-x}SiO_4:Eu_x$ (BOSE, including both BOSE yellow and BOSE green varieties, including for example $(Ba,Sr)_2SiO_4:Eu^{2+}$); and CASN $(CaAlSiN_3:Eu^{2+})$, and KSF narrowband red $(K_2SiF_6:Mn^{4+})$. Further examples include cyan or cyan/green phosphors (e.g., having a peak wavelength in a range of from 485 nm to 530 nm), red/orange or amber phosphors (e.g., having a peak wavelength in a range of from 575 nm to 595 nm), and narrowband red phosphors (e.g., having a peak wavelength in a range of from 605 nm to 640 nm). In certain embodiments, two or more phosphors may be mixed or provided in one or more discrete regions of a single lighting device.

In certain embodiments, at least one lumiphoric material may be spatially segregated ("remote") from and arranged to receive emissions from at least one electrically activated solid state emitter, with such spatial separation reducing thermal coupling between a solid state emitter and lumiphoric material. In certain embodiments, a spatially segregated lumiphor may be arranged to fully cover one or more electrically activated emitters of a lighting device. In certain embodiments, a spatially segregated lumiphor may be arranged to cover only a portion or subset of one or more electrically activated emitters.

In certain embodiments, at least one lumiphoric material may be arranged with a substantially constant thickness and/or concentration relative to different electrically activated emitters. In certain embodiments, one or more lumiphoric materials may be arranged with a presence, thickness, and/or concentration that vary relative to different emitters. Multiple lumiphors (e.g., lumiphors of different compositions) may be applied with different concentrations or thicknesses relative to different electrically activated emitters. In one embodiment, lumiphor presence, composition, thickness and/or concentration may vary relative to multiple electrically activated emitters. In certain embodiments, at least one lumiphoric material may be applied to a solid state emitter or a lumiphoric material support surface by patterning, which may be aided by one or more masks.

Various substrates may be used as mounting elements on which, in which, or over which multiple solid state light emitters (e.g., emitter chips) may be arranged or supported (e.g., mounted). Exemplary substrates may have electrical traces arranged on one or multiple surfaces thereof. A substrate, mounting plate, or other support element may include a printed circuit board (PCB), a metal core printed circuit board (MCPCB), a flexible printed circuit board, a dielectric laminate (e.g., FR-4 boards as known in the art) or any suitable substrate for mounting LED chips and/or LED packages.

In certain embodiments, one or more LED components can include one or more "chip-on-board" (COB) LED chips and/or packaged LED chips that can be electrically coupled or connected in series or parallel with one another and mounted on a portion of a substrate. In certain embodiments, COB LED chips can be mounted directly on portions of substrate without the need for additional packaging.

Certain embodiments may involve use of solid state emitter packages. A solid state emitter package may include at least one solid state emitter chip that is enclosed with packaging elements to provide environmental protection, mechanical protection, color selection, and/or light focusing utility, as well as electrical leads, contacts, and/or traces enabling electrical connection to an external circuit. One or more emitter chips may be arranged to stimulate one or more lumiphoric materials, which may be coated on, arranged over, or otherwise disposed in a light receiving relationship to one or more solid state emitters. At least one lumiphoric material may be arranged to receive emissions of at least some emitters of a plurality of solid state light emitters and responsively emit lumiphor emissions. A lens and/or encapsulant material, optionally including lumiphoric material, may be disposed over solid state emitters, lumiphoric materials, and/or lumiphor-containing layers in a solid state emitter package.

In certain embodiments, a lighting device as disclosed herein (whether or not including one or more LED packages) may include at least one of the following items arranged to receive light from at least one electrically activated solid state light emitter (e.g., LED): a single leadframe arranged to conduct electrical power to the at least one electrically activated solid state light emitter; a single reflector arranged to reflect at least a portion of light emanating from the at least one electrically activated solid state light emitter; a single submount or mounting element supporting the at least one electrically activated solid state light emitter; a single lens arranged to transmit at least a portion of light emanating from the at least one electrically activated solid state light emitter; and a single diffuser arranged to diffuse at least a portion of light emanating from the at least one electrically activated solid state light emitter.

In certain embodiments, a lighting device apparatus including multiple electrically activated solid state light emitters may include at least one of the following items arranged to receive light from the multiple emitters: multiple lenses, multiple optical elements, and/or multiple reflectors. Examples of optical elements include, but are not limited to, elements arranged to affect light mixing, focusing, collimation, dispersion, and/or beam shaping.

In certain embodiments, a solid state lighting device (e.g., package) may include a wall or cup (e.g., a reflector cup) defining a cavity, at least one solid state emitter arranged within the cavity, and encapsulant material arranged within the cavity. In certain embodiments, at least one solid state emitter may be arranged over a substrate and at least partially surrounded by a boundary wall (optionally embodying at least one dispensed dam material laterally spaced from the at least one emitter), with an encapsulant material arranged over the at least one emitter and in contact with the boundary wall.

The expressions "lighting device," "light emitting device," and "light emitting apparatus" as used herein are not limited, except that such elements are capable of emitting light. That is, a lighting device or light emitting apparatus can be a device which illuminates an area or volume, e.g., a structure, a swimming pool or spa, a room, a warehouse, an indicator, a road, a parking lot, a vehicle (either interior or exterior), signage (e.g., road signs), a billboard, a ship, a toy, a mirror, a vessel, an electronic device, a boat, an aircraft, a stadium, a computer, a remote audio device, a remote video device, a cell phone, a tree, a window, an LCD display, a cave, a tunnel, a yard, a lamppost, or a device or array of devices that illuminate an enclosure, or a device that is used for edge or back-lighting (e.g., backlight poster, signage, LCD displays), light bulbs, bulb replacements (e.g., for replacing incandescent lights, low voltage lights, fluorescent lights, etc.), outdoor lighting, street lighting, security lighting, exterior residential lighting (wall mounts, post/column mounts), ceiling fixtures/wall sconces, under cabinet lighting, lamps (floor and/or table and/or desk), landscape lighting, track lighting, task lighting, specialty lighting, ceiling fan lighting, archival/art display lighting, high vibration/impact lighting (work lights, etc.), mirrors/vanity lighting, personal lighting device (e.g., flashlight), or any other light emitting devices. In certain embodiments, lighting devices or light emitting apparatuses as disclosed herein may be self-ballasted. In certain embodiments, a light emitting apparatus may be embodied in a light fixture.

Subject matter herein relates in certain embodiments to illuminating an object, space, or enclosure using at least one lighting device or lighting apparatus as disclosed herein, optionally by energizing a single power line connected to multiple lighting devices and/or by pulse width modulation control of the at least one lighting device or lighting apparatus.

Subject matter herein relates in certain embodiments to an illuminated enclosure (the volume of which can be illuminated uniformly or non-uniformly), comprising an enclosed space and at least one lighting device as disclosed herein, wherein the at least one lighting device illuminates at least a portion of the enclosure (uniformly or non-uniformly). Subject matter herein further relates to an illuminated area comprising at least one item selected from among the group consisting of a structure, a swimming pool or spa, a room, a warehouse, an indicator, a road, a parking lot, a vehicle, signage (e.g., road signs), a billboard, a ship, a toy, a mirror, a vessel, an electronic device, a boat, an aircraft, a stadium, a computer, a remote audio device, a remote video device, a cell phone, a tree, a window, a LCD display, a cave, a tunnel, a yard, a lamppost, etc., having mounted therein or thereon at least one lighting device or light emitting apparatus as described herein. Methods including illuminating an object, a space, or an environment utilizing one or more lighting devices are disclosed herein. In certain embodiments, a lighting apparatus as disclosed herein includes multiple LED components arranged in an array (e.g., a one-dimensional or two-dimensional array).

Aspects disclosed herein relate to solid state lighting devices with melatonin suppression characteristics that ameliorate or reduce symptoms of circadian rhythm disorders or other health conditions in humans, as well as plants and animals. As noted previously, it is principally blue light (e.g., including blue light at a peak wavelength value between 460 nm to 480 nm, with some activity from about 360 nm to about 600 nm), that suppresses melatonin, such that a reduction in the proportion of blue content (e.g., peak wavelength between 460 nm to 480 nm) of aggregate emissions will tend to reduce melatonin suppression. Aspects disclosed herein additionally relate to providing one or more of the foregoing effects while maintaining color rendering index (CRI) values acceptably high for the intended use, as well as providing lighting devices with high luminous efficacy and enhanced energy efficiency. Certain aspects disclosed herein relate to solid state lighting devices for outdoor applications with characteristics that reduce light pollution. Light from outdoor lighting devices can be reflected off of various surfaces including the ground and the sides of buildings toward the sky. Blue light tends to be scattered more prominently by molecules in the atmosphere and can result in a diffuse glow that obscures the night sky. Additionally, high levels of blue light during the night may disrupt circadian rhythms of humans, plants, and animals. Certain aspects disclosed herein relate to solid state lighting devices for outdoor lighting applications with reduced light pollution and a lower impact on circadian rhythms while maintaining CRI values acceptably high for the intended use, as well as providing lighting devices with high luminous efficacy and enhanced energy efficiency.

Gas-discharge lamps, such as low-pressure sodium (LPS) lamps and high-pressure sodium (HPS) lamps, have been widely used for outdoor lighting applications including street lamps and garage lighting. LPS and HPS lights typically emit light having yellow, orange, or red characteristics with a correlated color temperature (CCT) around 2200 Kelvin (K) or below. The spectral distribution of LPS and HPS lights is notably lacking emissions in a blue spectral range and therefore typically do not have an impact on melatonin suppression. However, gas-discharge lamps are also known for having very poor CRI values, such as 25 or below. Accordingly, detecting color differences between objects illuminated by gas-discharge lights is difficult.

FIG. 5A is a plot of a circadian stimulus (CS) model versus CCT for various light sources including representative HPS and LPS light sources, a LED with lumiphoric materials, and a red LED. The CS model is a metric developed by the Lighting Research Center (LRC) at Rensselaer Polytechnic Institute that characterizes how light affects the human circadian system. The CS value is related to an amount of melatonin suppression. For example, a higher CS value (e.g. 0.3) indicates light having greater amounts of radiation that may result in higher melatonin suppression (~30%) in humans. Such radiation may include, but is not limited to, short wavelength radiation that includes blue and/or green emissions. The red LED is plotted for reference and has a CS value of about 0. The representative LPS light source has the next lowest CS value and a CCT below 1900 K. Several representative HPS light sources are plotted along with various LEDs that include phosphor materials. The various LEDs all include at least one blue LED configured to stimulate emissions from a YAG phosphor and a nitride red phosphor. The various LEDs were configured to have different CCT values, but the same CRI of at least 65. Notably, LEDs with phosphor materials and CRI values of at least 65 are able to match the (low) CS values of HPS light sources. In addition to higher CRI values, LEDs may provide improved lumens per watt efficiency.

FIG. 5B is a plot of a melanopic lux model versus CCT for the same light sources plotted in FIG. 5A. The melanopic lux model, or melanopic illuminance, provides a measurement of the amount of light that activates the melanopsin signaling system in humans. Melanopsin photoreceptors in the eye are sensitive to a range of wavelengths, and a peak light absorption occurs at blue wavelengths around 480 nm. Accordingly, in FIG. 5B, the melanopic lux value is related to the amount of blue light present in the various light sources. A higher melanopic lux value indicates higher melanopic suppression in humans. As with the CS model, LEDs with phosphor materials and CRI values of at least 65 are able to match melanoptic lux values of HPS light sources.

Figure 6A:
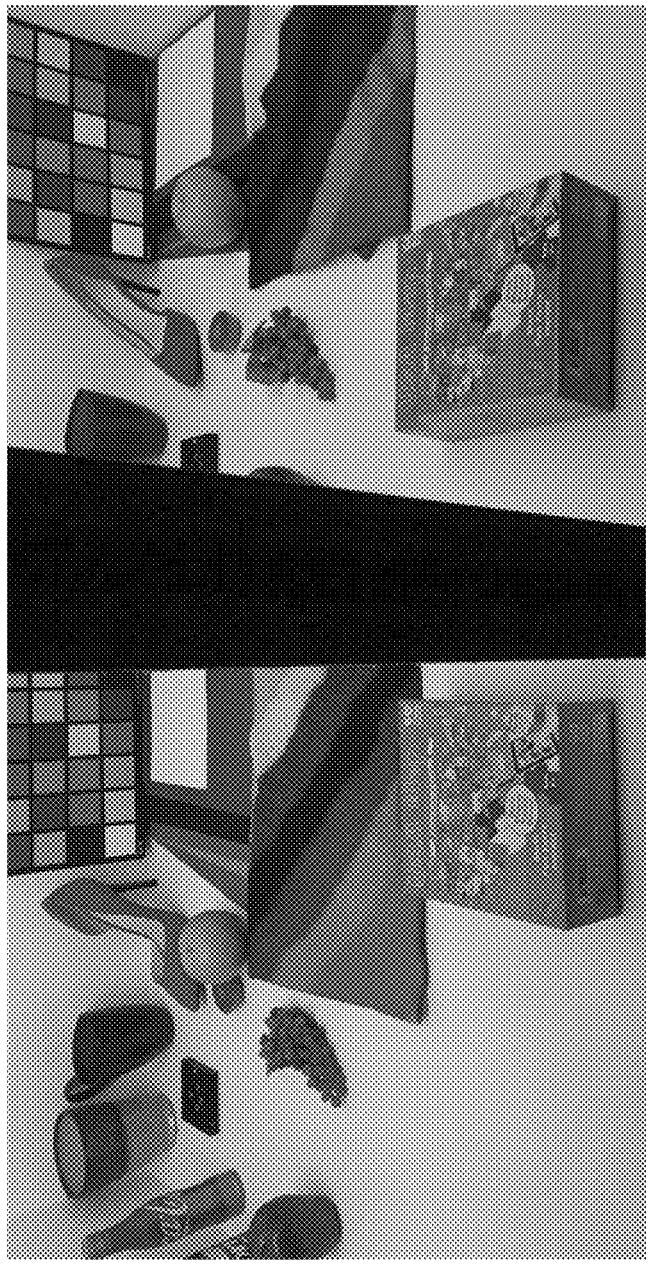
FIG. 6A is a photograph of two side-by-side test booths containing colored objects, with the left booth being subject to illumination with a LED light source (including a blue LED and multiple phosphors) and the right booth being subject to illumination with a representative HPS light source.

FIG. 6A is a photograph of two side-by-side test booths containing colored objects, with the left booth being subject to illumination with a LED light source (including a blue LED and multiple phosphors) and the right booth being subject to illumination with a representative HPS light source. The LED light source is configured with a CRI of about 70 and a CCT of about 2200 K. For a comparable illuminance level, the LED light source shows notably superior color rendering. FIG. 6B provides spectral power distribution plots (in normalized intensity versus wavelength) for the two light sources of FIG. 6A. As shown, a majority of higher light intensities occur around or slightly above 580 nm for both light sources. However, the LED light source includes a noticeably wider emission spectrum, as high as about 680 nm and as low as about 500 nm, due to broad emissions from the phosphor materials; accordingly, the LED light source has a superior CRI value. FIG. 6C is a table listing various performance characteristics for the two light sources of FIG. 6A. Notably, the average CRI, or CRI Ra, for the LED light source is 73 compared to a value of 9 for the HPS light source. The CCT of the LED light source used was slightly higher than the CCT of the HPS light source. Accordingly, the melanopic perceived brightness percent (MPB %), the circadian light (CLA), and melanopic lux were also higher than the HPS light used, but still comparable with normal ranges for typical HPS light sources. The Duv for both light sources is within 0.004 of the blackbody locus (BBL). Additionally, the luminaire efficiency rating (LER) is comparable for the two light sources while the R9 values are higher for the LED light source.

As described above, solid state lighting devices may be configured to provide lighting characteristics and melatonin suppression characteristics similar to gas-discharge light sources, but with superior color rendering. In some aspects described herein, a solid state lighting device may be configured with differences in additional lighting characteristics to provide a further-improved replacement for a gas-discharge light source. In some embodiments, a solid state lighting device is configured to provide aggregate emissions having a color point that is off the BBL in a manner that departs from conventional industry tolerances, such as a Duv that is at least 0.005. As described herein, a solid state lighting source with a CCT targeting gas-discharge applications may be configured to provide a color point off the BBL with a Duv value of at least 0.005 to provide lighting characteristics that include a further reduced CS value and increased efficacy while still maintaining a high CRI.

FIG. 7A provides a portion of a 1931 CIE diagram illustrating the relationship of various solid state lighting sources to the BBL. Each of the solid state lighting devices are modeled to provide a CRI of at least 65 and include a blue LED with a mixture of YAG and red phosphors. In particular, the CRI of the solid state lighting devices is in a range of about 65 and 75. The phosphor mixture was varied between the solid state lighting sources to provide data points across a range of CCT values. Additionally, solid state lighting sources for four of the CCT values were modeled with increasing Duv values. For example, dashed line 10 circles three data points having a CCT of about 2250 and Duv values of 0 (black circle on the BBL), 0.005 (white circle above the BBL), and 0.010 (white circle further above the BBL), respectively. A Duv value of 0.005 corresponds to about a 5-step MacAdam ellipse above the BBL, and a Duv value of 0.010 corresponds to about a 10-step MacAdam ellipse above the BBL. FIG. 7B is a plot comparing CS values by CCT for each of the data points of FIG. 7A. For CCT values less than about 2600, the data points on the BBL have CS values that compare favorably to HPS light sources. Additionally, the CS values are further decreased for data points with increased Duv values. For example, dashed line 12 circles the same three data points as dashed line 10 of FIG. 7A. For CCT values of about 2250, the CS value progressively decreases (corresponding to reduced melatonin suppression) as the Duv increases for each data point. Accordingly, a solid state lighting device may be configured with Duv values outside of conventional tolerances to provide a replacement for HPS light sources that includes a similar CCT, a similar or lower CS value, and a higher CRI.

FIG. 7C is a table listing the various characteristics for each of the data points plotted in FIG. 7A and FIG. 7B. In the table, rows with data points on the BBL (Duv of 0) are shaded. The unshaded rows below each shaded row represent data points with the same CCT and increasing Duv values. Each of the solid state lighting devices have CRI values in a range of 65 and 75. In addition to CS and CLA, other lighting characteristics in the table include luminaire efficiency rating (LER), CRI, fidelity index (Rf), relative-gamut index (Rg), R9 prime (R9'), luminous flux (Lx), gamut area index (Qg), lumens per watt (LPW), and Amelv (a value that is proportional to melanopic lux). (R9' is the same as R9 for values less than 100 (as shown in FIG. 7C), but is capable of increasing above 100 for an "oversaturated" condition.) Notably, for each group of CCT values (e.g. 2000, 2250, 2500, and 2750), the CS and CLA values decrease with each increase in Duv and the LER and the LPW values increase.

Accordingly, in some embodiments, a solid state lighting device comprises a first electrically activated solid state emitter, a first lumiphoric material arranged to receive at least a portion of emissions of the first electrically activated solid state emitter and responsively generate first lumiphor emissions, and at least one other light emitter including at least one of the following items (a) or (b): (a) a second electrically activated solid state emitter, or (b) a second lumiphoric material arranged to receive at least a portion of emissions of the first electrically activated solid state emitter and responsively generate second lumiphor emissions.

Aggregated emissions of the solid state lighting device include at least a portion of the emissions of each of the first electrically activated solid state emitter, the first lumiphoric material, and the at least one other light emitter and have a circadian stimulus (CS) value of less than 0.17, and have a Duv of at least 0.005. In some embodiments, the aggregated emissions have a CCT of about 2000K (or in a range of 1950K to 2050K), and a CS value of less than 0.125 (or in a range from 0.125 to 0.110). In other embodiments, a solid state lighting device comprises a CCT of about 2250K (or in a range of 2200K to 2300K), and a CS value of less than 0.145 (or in a range from 0.145 to 0.12). In other embodiments, a solid state lighting device comprises a CCT of about 2550K (or in a range of 2450K to 2550K), and a CS value of less than 0.17 (or in a range from 0.17 to 0.13). As previously described and shown in FIG. 7C, the solid state lighting devices having the CCT and CS values described above comprise a CRI that is at least 65; or in a range of 65 to 75.

As also shown in FIG. 7C, in some embodiments, a solid state lighting device comprises a CCT of about 2000K (or in a range of 1950K to 2050K), and an LER value of at least 325 (or in a range from 325 to 330). In other embodiments, a solid state lighting device comprises a CCT of about 2250K (or in a range of 2200K to 2300K), and an LER value of at least 335 (or in a range from 335 to 355). In other embodiments, a solid state lighting device comprises a CCT of about 2550K (or in a range of 2450K to 2550K), and an LER value of at least 340 (or in a range from 340 to 370). As previously described and shown in FIG. 7C, the solid state lighting devices having the CCT and LER values described above comprise a CRI that is at least 65; or in a range of 65 to 75.

Additionally, multiple data points have LPW values that meet the technical requirements for efficiency of indoor and outdoor luminaires to qualify for the DesignLights Consortium (DCL) Premium classification, version 4.3 as of Mar. 26, 2018. For example, the DLC Premium requirement (version 4.3) for minimum efficiency of "Outdoor—High Output" luminaires is 120 LPW; and the DLC Premium requirement (version 4.3) for minimum efficiency of "Outdoor—Mid Output" luminaires is 115 LPW.

Accordingly, in some embodiments, a solid state lighting device comprises at least one electrically activated solid state emitter configured to generate emissions having a peak wavelength in a blue range, such as 430 nm to 480 nm; a first lumiphoric material arranged to receive at least a portion of the emissions of the at least one electrically activated solid state emitter and responsively generate first lumiphor emissions having a peak wavelength in a green/yellow range, such as 540 nm to 570 nm; and a second lumiphoric material arranged to receive at least a portion of the emissions of the at least one electrically activated solid state emitter and responsively generate second lumiphor emissions having a peak wavelength in a red range, such as 605 nm to 650 nm. Aggregated emissions of the solid state lighting device include at least a portion of emissions of each of the electrically activated solid state emitter, the first lumiphor emissions, and the second lumiphor emissions. In some embodiments, the aggregated emissions have a CCT in a range of from 1800 K to 2600 K, and have a Duv of at least 0.005. In further embodiments, the aggregated emissions have a CCT in a range of about 1800 K to 2300 K; and in still further embodiments, the aggregated emissions have a CCT in a range of about 2150 K to 2250 K. In some embodiments, the aggregated emissions have a Duv in a range from 0.005 to 0.020; in further embodiments, the aggregated emissions have a Duv in a range from 0.005 to 0.015; and in still further embodiments, the aggregated emissions have a Duv in a range from 0.005 to 0.010. In some embodiments, the aggregated emissions have a CRI of at least 65. In further embodiments, the aggregated emissions have a CRI of at least 70. In further embodiments, the aggregated emissions have a CRI in a range of 65 to 85, or in a range of 65 to 80, or in a range of 65 to 85, or in a range of 70 to 90, or in a range of 70 to 80.

In some embodiments, the aggregated emissions may include additional solid state emitters or additional lumiphoric materials. For example, in some aspects, solid state lighting device comprises a first electrically activated solid state emitter; a first lumiphoric material arranged to receive at least a portion of emissions of the first electrically activated solid state emitter and responsively generate first lumiphor emissions; a second electrically activated solid state emitter; and a second lumiphoric material arranged to receive at least a portion of emissions of the second electrically activated solid state emitter and responsively generate second lumiphor emissions, wherein the second lumiphor emissions have a peak wavelength that differs from a peak wavelength of the first lumiphor emissions by at least 25 nm. Aggregated emissions of the solid state lighting device include at least a portion of the emissions of each of the first electrically activated solid state emitter, the second electrically activated solid state emitter, the first lumiphor emissions, and the second lumiphor emissions. In some embodiments, the aggregated emissions have a correlated color temperature (CCT) in a range of from 1800 Kelvin (K) to 2600 K, and have a Duv of at least 0.005. In some embodiments, the second lumiphor emissions have a peak wavelength that differs from the peak wavelength of the first lumiphor emissions by at least 35 nm, or by at least 55 nm, or by at least 75 nm, or in a range of about 35 nm to about 105 nm. In some embodiments, the first electrically activated solid state emitter is configured to generate emissions having a peak wavelength in a range from 430 nm to 480 nm and the first lumiphor emissions have a peak wavelength in a range from 540 nm to 570 nm; and the second electrically activated solid state emitter is configured to generate emissions having a peak wavelength in a range from 430 nm to 480 nm and the second lumiphor emissions have a peak wavelength in a range from 605 nm to 650 nm. In some embodiments, the aggregated emissions have a CRI of at least 65. In further embodiments, the aggregated emissions have a CRI of at least 70. In further embodiments, the aggregated emissions have a CRI in a range of 65 to 85, or in a range of 65 to 80, or in a range of 65 to 85, or in a range of 70 to 90, or in a range of 70 to 80. The aggregated emissions may have additional CCT and Duv values as described in previous embodiments.

In some embodiments, a solid state lighting device may comprise an electrically activated first solid state emitter configured to generate emissions having a peak wavelength in a range from 430 nm to 480 nm; an electrically activated second solid state emitter configured to generate emissions having a peak wavelength in a range from 605 nm to 650 nm; and a first lumiphoric material arranged to receive at least a portion of the emissions from at least one of the first solid state emitter and the second solid state emitter and responsively generate first lumiphor emissions having a peak wavelength in a range from 540 nm to 570 nm. The aggregated emissions from the first and second solid state emitters and the first and second lumiphor emissions may have a CCT in a range of from 1800 K to 2600 K and may have a Duv of at least 0.005. Optionally, the solid state lighting device may further include a second lumiphoric material arranged to receive at least a portion of the emissions from at least one of the first solid state emitter and the second solid state emitter and responsively generate second lumiphor emissions having a peak wavelength in a range from 605 nm to 650 nm. In further embodiments, the peak wavelength of the second solid state emitter is different from the peak wavelength of the second lumiphoric material within the range from 605 nm to 650 nm.

In some embodiments, at least one of the first lumiphoric material and the second lumiphoric material of previous embodiments may include a plurality of lumiphoric materials. For example, the first lumiphoric material may comprise two different lumiphoric materials configured to generate emissions having two different peak wavelengths within a range from 540 nm to 570 nm. In a similar manner, the second lumiphoric material may comprise two different lumiphoric materials configured to generate emissions having two different peak wavelengths within a range from 605 nm to 650 nm.

In some embodiments, the first and second lumiphoric materials are dispersed together in a common binder, such as silicone. In other embodiments, the first and second lumiphoric materials are arranged in discrete layers. For example, the second lumiphoric material configured to generate second lumiphor emissions having a peak wavelength in a range from 605 nm to 650 nm may be arranged between the first solid state emitter and the first lumiphoric material configured to generate first lumiphor emissions having a peak wavelength in a range from 540 nm to 570 nm. In that regard, for embodiments where the first lumiphor emissions include wavelengths within the excitation spectrum of the second lumiphoric material, the amount of first lumiphor emissions received by the second lumiphoric material may be reduced, thereby improving efficiency.

Having described desirable combinations of solid state emitters and lumiphoric materials, solid state lighting devices that may incorporate such emitters and lumiphoric materials will now be described. In some embodiments, the first lumiphoric material and the second lumiphoric material are spatially separated from one another. In some embodiments, the first lumiphoric material and the second lumiphoric material are spatially separated from the at least one solid state emitter.

In certain embodiments, one or more solid state emitters and lumiphoric materials as previously described may be provided in a single-chip or multi-chip LED package as described below for FIGS. 8-15.

Figure 8:
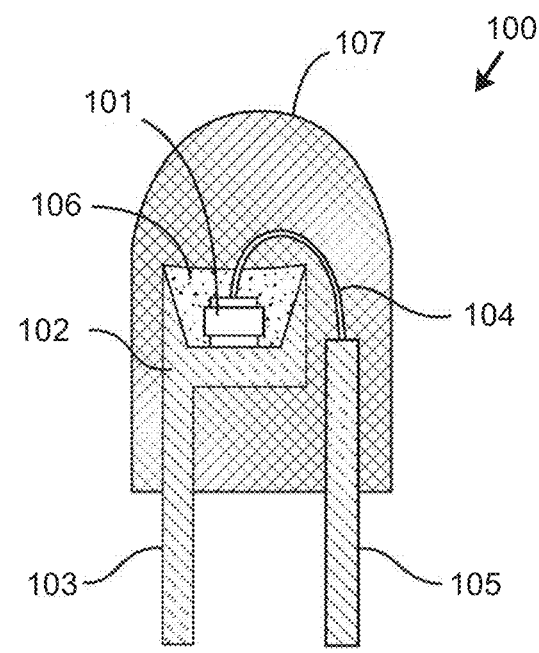
FIG. 8 is a schematic cross-sectional view of a first exemplary LED that may embody (or may be incorporated in) a lighting device according to one embodiment of the present disclosure.

FIG. 8 illustrates a LED package 100 including a single LED chip 101 mounted on a reflective cup 102 using solder or a conductive epoxy, such that ohmic contacts for a cathode (or an anode) of the LED chip 101 are electrically coupled to the bottom of the reflective cup 102. The reflective cup 102 is either coupled to or integrally formed with a first lead 103 of the LED package 100. One or more bond wires 104 connect the ohmic contacts for the anode (or cathode) of the LED chip 101 to a second lead 105. The reflective cup 102 may be filled with an encapsulant material 106 that encapsulates the LED chip 101. The encapsulant material 106 may be clear or contain one or more wavelength conversion materials, such as phosphors or other lumiphoric materials. The entire assembly is encapsulated in a clear protective resin 107, which may be molded in the shape of a lens to control light emitted from the LED chip 101 and any lumiphoric material(s) contained in the reflective cup 102.

Figure 9:
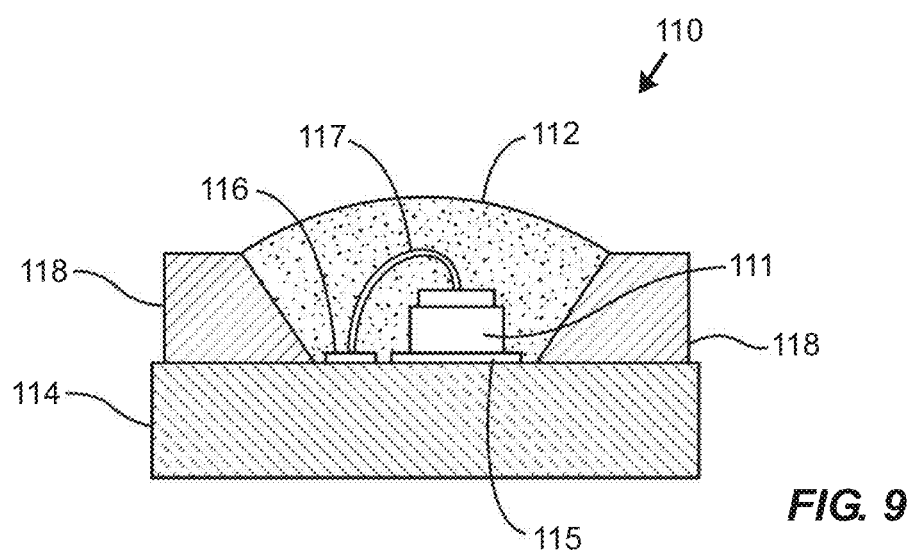
FIG. 9 is a schematic cross-sectional view of a second exemplary LED that may embody (or may be incorporated in) a lighting device according to one embodiment of the present disclosure.

An alternative LED package 110 is illustrated in FIG. 9 wherein a LED chip 111 is mounted on a substrate 114. Ohmic contacts for an anode (or cathode) of the LED chip 111 are directly mounted to first contact pads 115 on a surface of the substrate 114. The ohmic contacts for the cathode (or anode) of the LED chip 111 are connected to second contact pads 116, which are also on the surface of the substrate 114, using bond wires 117. The LED chip 111 resides in a cavity of a reflector structure 118, which is formed from a reflective material and functions to reflect light emitted from the LED chip 111 through the opening formed by the reflector structure 118. The cavity formed by the reflector structure 118 may be filled with an encapsulant material 112 that encapsulates the LED chip 111. The encapsulant material 112 may be clear or contain at least one wavelength conversion material, such as one or more phosphors or other lumiphoric materials.

FIGS. 10A-13B illustrate exemplary portions of solid state lighting devices in different configurations incorporating electrically activated solid state light emitters and lumiphoric materials arranged over package mounts (or other substrates) and optionally overlaid with lenses, wherein such devices may be used alone or in groups according to certain embodiments described herein. It is to be appreciated that various structures employed within complete lighting devices (e.g., package leads, leadframes, contacts, wirebonds, bond structures, heat transfer elements, diffusers, additional reflecting surfaces, power supplies, and the like) have been omitted for clarity of illustration, but one skilled in the art would appreciate that known structures could be incorporated in operative lighting devices including the illustrative portions provided in FIGS. 16A-19B.

Figure 10A:
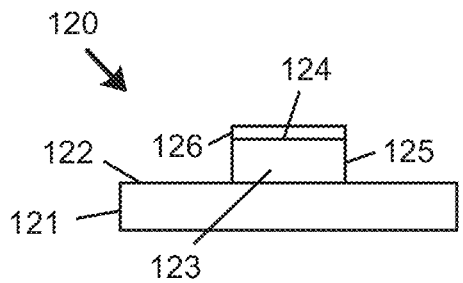
FIG. 10A is a side cross-sectional schematic view of at least a portion of a solid state light emitting device including a solid state emitter chip arranged over a package mount, with a top surface of the emitter chip being covered with a wavelength conversion material.

FIG. 10A illustrates a solid state light emitting device 120 including at least one solid state emitter (e.g., LED) chip 123 (which may include LED epitaxial layers and a support) arranged over an upper surface 122 of a package mount (or other substrate such as a printed circuit board) 121, with a top surface 124 of the solid state emitter chip 123 being covered with at least one lumiphoric material 126 (e.g., a mixture or dispersion of different lumiphoric materials as disclosed herein). The package mount 121 may include metalized regions and/or vias (not shown) for conduction of electrical signals to the solid state emitter chip 123. Side surfaces 125 of the solid state emitter chip 123 may be exposed, or in certain embodiments may be coated with one or more materials or an encapsulant.

Figure 10B:
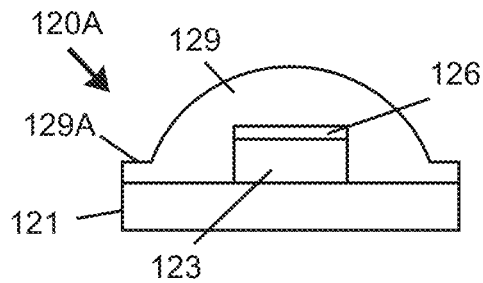
FIG. 10B is a side cross-sectional schematic view of at least a portion of a solid state light emitting device including the device of FIG. 16A with the addition of a curved (e.g., hemispherical) lens.

FIG. 10B illustrates a solid state light emitting device 120A including the device 120 of FIG. 10A following the addition of a lens 129 having a curved (e.g., substantially hemispherical) shape. The lens 129 may be formed by any suitable method, including but not limited to molding using silicone material. In certain embodiments, the lens 129 may have a width or lateral extent that is substantially equal to a width or lateral extent of the package mount 121, and a peripheral portion 129A of the lens 129 may have a substantially uniform thickness. In other embodiments, the lens 129 may have a width or lateral extent that is less than the width or lateral extent of the package mount 121.

Figure 11A:
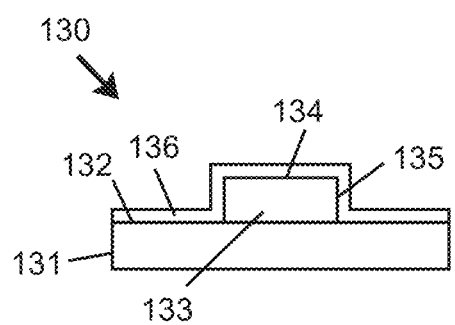
FIG. 11A is a side cross-sectional schematic view of at least a portion of a solid state light emitting device including a solid state emitter chip arranged over a package mount, with top and side surfaces of the emitter chip and an upper surface of the package mount being covered with a wavelength conversion material.

FIG. 11A illustrates a solid state light emitting device 130 including a solid state emitter (e.g., LED) chip 133 (which may include LED epitaxial layers and a support) arranged over an upper surface 132 of a package mount (or other substrate such as a printed circuit board) 131, with a top surface 134 and side surfaces 135 of the solid state emitter chip 133, as well as at least a portion of the upper surface 132 of the package mount 131, being covered with a wavelength conversion (e.g., lumiphoric) material 136. In certain embodiments, the solid state emitter chip 133 may be mounted to the package mount 131, and thereafter the solid state emitter chip 133 and the upper surface 132 of the package mount 131 may be coated with the lumiphoric material 136. Coating may be performed according to any suitable process disclosed herein, such as spray coating, dipping, or the like. The lumiphoric material 136 may be arranged in a conformal layer that follows the shape and outline of multiple surfaces of the solid state emitter chip 133. Electrical connections to the solid state emitter chip 133 may be made either before or after coating steps.

Figure 11B:
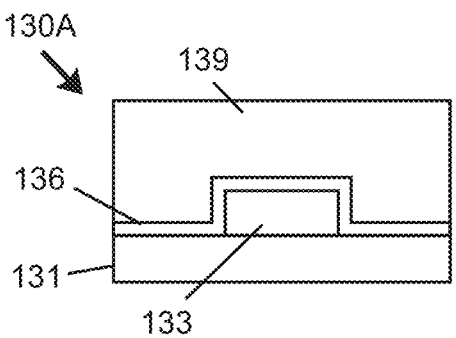
FIG. 11B is a side cross-sectional schematic view of at least a portion of a solid state light emitting device including the device of FIG. 17A with the addition of a lens having a substantially rectangular cross-sectional shape.

FIG. 11B illustrates a solid state light emitting device 130A including the device 130 of FIG. 11A following the addition of a lens 139 having a substantially rectangular cross-sectional curved (e.g., substantially hemispherical) shape. The lens 139 may be formed by any suitable method, including but not limited to molding using silicone material. In certain embodiments, the lens 139 may have a width or lateral extent that is substantially equal to a width or lateral extent of the package mount 131. In other embodiments, the lens 139 may have a width or lateral extent that is less than the width or lateral extent of the package mount 131.

Figure 12A:
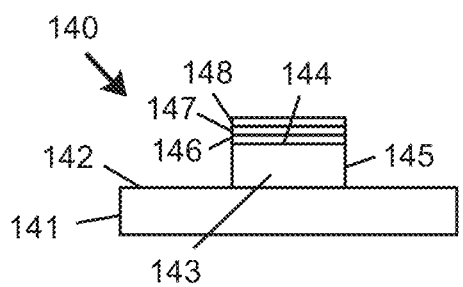
FIG. 12A is a side cross-sectional schematic view of at least a portion of a solid state light emitting device including a solid state emitter chip arranged over a package mount, with a top surface of the emitter chip being covered with at least one wavelength conversion material layer.

FIG. 12A illustrates a solid state light emitting device 140 including a solid state emitter (e.g., LED) chip 143 (which may include LED epitaxial layers and a support) arranged over an upper surface 142 of a package mount (or other substrate such as a printed circuit board) 141, with a top surface 144 of the solid state emitter chip 143 being covered with first through third lumiphoric material layers 146, 147, 148. In some embodiments, the solid state emitter chip 143 is covered with the first and second lumiphoric material layers 146, 147 and the third lumiphoric material layer 148 is omitted. The package mount 141 may include metalized regions and/or vias (not shown) for conduction of electrical signals to the solid state emitter chip 143. Side surfaces 145 of the solid state emitter chip 143 may be exposed or otherwise coated with lumiphoric material. In certain embodiments, the solid state emitter chip 143 may be coated with the first through third lumiphoric material layers 146, 147, 148, and thereafter the pre-coated solid state emitter chip 143 may be mounted to the package mount 141 followed by establishment of suitable electrically conductive connection(s) to the solid state emitter chip 143. Coating may be performed according to any suitable process disclosed herein, such as spray coating.

Figure 12B:
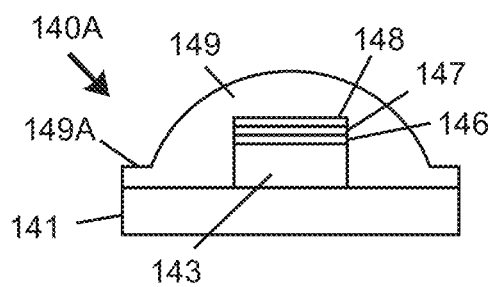
FIG. 12B is a side cross-sectional schematic view of at least a portion of a solid state light emitting device including the device of FIG. 18A with the addition of a curved (e.g., hemispherical) lens.

FIG. 12B illustrates a solid state light emitting device 140A including the device 140 of FIG. 12A following the addition of a lens 149 having a curved (e.g., substantially hemispherical) shape. The lens 149 may be formed by any suitable method, including but not limited to molding using silicone material. In certain embodiments, the lens 149 may have a width or lateral extent that is substantially equal to a width or lateral extent of the package mount 141, and a peripheral portion 149A of the lens 149 may have a substantially uniform thickness. In other embodiments, the lens 149 may have a width or lateral extent that is less than the width or lateral extent of the package mount 141.

Figure 13A:
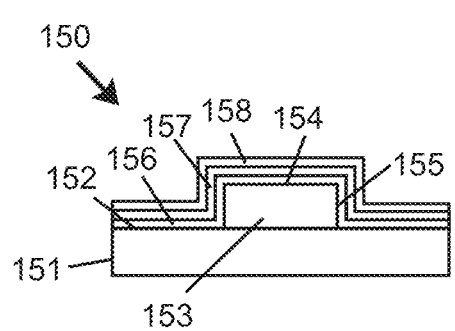
FIG. 13A is a side cross-sectional schematic view of at least a portion of a solid state light emitting device including a solid state emitter chip arranged over a package mount, with top and side surfaces of the emitter chip and an upper surface of the package mount being covered with multiple wavelength conversion material layers.

FIG. 13A illustrates a solid state light emitting device 150 including a solid state emitter (e.g., LED) chip 153 (which may include LED epitaxial layers and a support) arranged over an upper surface 152 of a package mount (or other substrate such as a printed circuit board) 151, with a top surface 154 and side surfaces 155 of the solid state emitter chip 153, as well as an upper surface 152 of the package mount 151, being covered with first through third lumiphoric material layers 156, 157, 158. In some embodiments, the solid state emitter chip 153 is covered with the first and second lumiphoric material layers 156, 157 and the third lumiphoric material layer 158 is omitted. In certain embodiments, the solid state emitter chip 153 may be mounted to the package mount 151, and thereafter the LED chip 153 and the upper surface 152 of the package mount 151 may be coated with the lumiphoric material layers 156, 157, 158. Coating may be performed according to any suitable process disclosed herein, such as spray coating. The lumiphoric material layers 156, 157, 158 may be arranged in conformal layers that follow the shape and outline of multiple surfaces of the solid state emitter chip 153. Electrical connections to the solid state emitter chip 153 may be made either before or after coating steps.

Figure 13B:
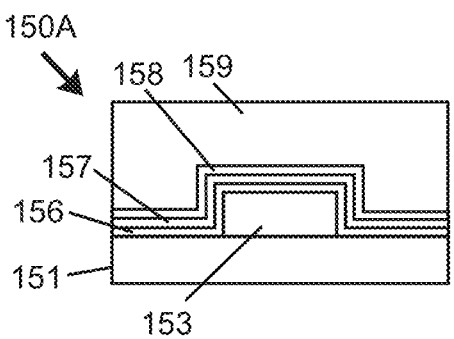
FIG. 13B is a side cross-sectional schematic view of at least a portion of a solid state light emitting device including the device of FIG. 19A with the addition of a lens having a substantially rectangular cross-sectional shape.

FIG. 13B illustrates a solid state light emitting device 150A including the device 150 of FIG. 13A following the addition of a lens 159 having a substantially rectangular cross-sectional curved (e.g., substantially hemispherical) shape. The lens 159 may be formed by any suitable method, including but not limited to molding using silicone material. In certain embodiments, the lens 159 may have a width or lateral extent that is substantially equal to a width or lateral extent of the package mount 151. In other embodiments, the lens 159 may have a width or lateral extent that is less than the width or lateral extent of the package mount 151.

Although specific lens shapes are illustrated in FIGS. 10B, 11B, 12B, and 13B, it is to be appreciated that lenses according to any suitable shapes may be applied to any of the lighting devices illustrated in FIGS. 10A-13B. For example, symmetric, non-symmetric, polygonal, truncated hemispherical, faceted, textured, and/or trench-defining lenses may be used.

Figure 14:
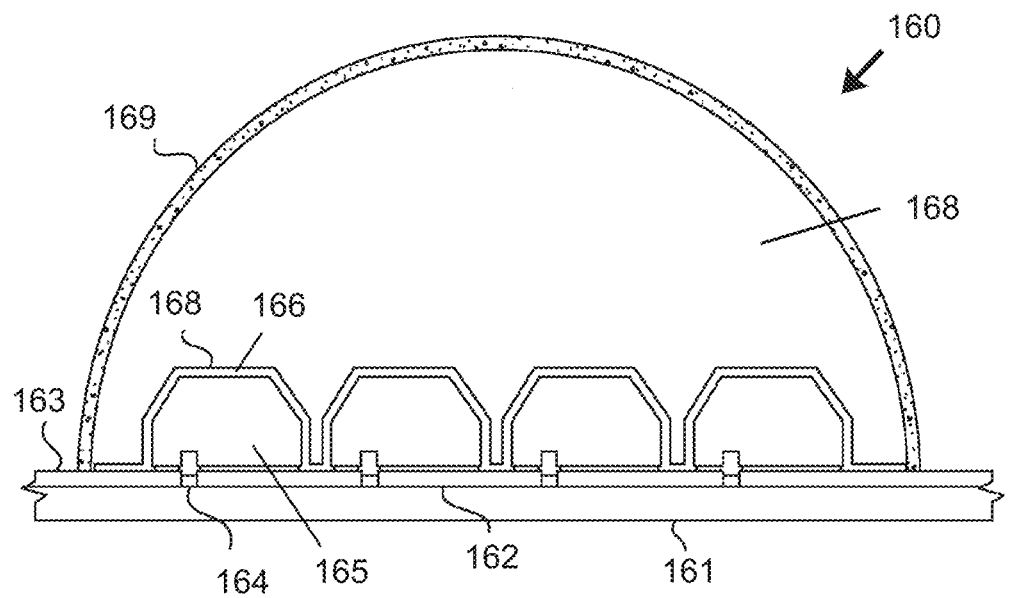
FIG. 14 is a side cross-sectional view of at least a portion of a solid state light emitting device including multiple solid state emitter chips coated with multiple lumiphoric materials and arranged under a hemispherical optical element.

FIG. 14 is a side cross-sectional view of at least a portion of a solid state light emitting device 160 including multiple solid state emitter (e.g., LED) chips 165 arranged over a submount 161 in a flip-chip configuration, with both anode and cathode connections on the bottom of the chips 165. The solid state emitter chips 165 may (optionally) include angled or beveled upper edges with a non-rectangular (e.g., polygonal) cross-section, with such shape serving to enhance light extraction. The solid state emitter chips 165 are coated or otherwise covered with one or more lumiphoric materials 166 (e.g., in one or more conformal layers) and arranged under a hemispherical optical element (e.g., lens) 169, with the conformal layer(s) 166 following the shape and contour of multiple surfaces of the solid state emitter chips 165 (preferably with substantially constant thickness). Such coating may be performed using any coating technique disclosed herein or otherwise known in the art. As shown in FIG. 14, the conformal layer(s) 166 may extend over, between and laterally beyond the solid state emitter chips 165 (such as over a reflective material disposed between or adjacent to the solid state emitter chips 165). The optical element 169 may be separated from the solid state emitter chips 165 via a gap or an intervening material 168, which may include an encapsulant or a fluid medium such as liquid or gel (e.g., mineral oil, perfluorinated polyether (PFPE) liquid, or other fluorinated or halogenated liquid or gel). The intervening material 168 may also include an index matching medium characterized by a refractive index that provides for reduced or minimal reflection or internal refraction of light emissions. In certain embodiments, elements 168, 169 may embody a single element, such as molded silicone. In certain embodiments, a thickness of each conformal layer 166 may be less than half the spacing between adjacent solid state emitter chips 165. In certain embodiments, spacing between the solid state emitter chips 165 may be on the order of 10 to 75 micrometers, although larger spacing (up to 150 or even 500 micrometers) may also be used. In certain embodiments, the optical element 169 may include one or more functional materials, such as lumiphoric material, filtering material, and/or scattering material, which may be doped, coated, or otherwise provided in or on the optical element 169. Still referring to FIG. 14, the submount 161 (e.g., alumina, aluminum nitride, high temperature polymers, etc.) is covered with a pattern of metal (e.g., traces) 163 that may be used to interconnect the solid state emitter chips 165 and provide connection to a power supply (not shown). The metal pattern 163 includes connection pads 162 with an insulating material 164 therebetween.

Figure 15:
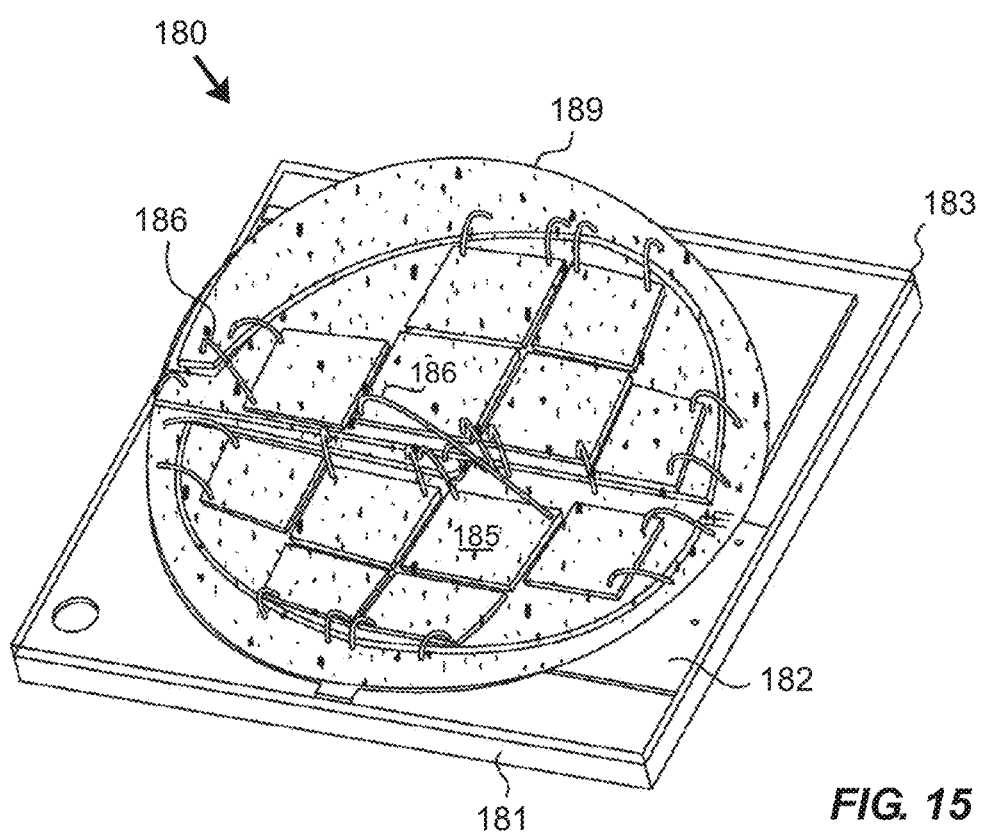
FIG. 15 is a perspective view of at least a portion of a solid state emitter package including multiple solid state emitter chips coated with multiple lumiphoric materials, with the chips coupled to electrical traces via wirebonds and arranged under a hemispherical optical element.

FIG. 15 illustrates a solid state emitter package 180 including multiple solid state emitter (e.g., LED) chips 185 coupled to electrical traces or metal patterns 182 via wirebonds 186 and arranged under a hemispherical optical element (e.g., lens) 189. In certain embodiments, one or more solid state emitter chips 185 are coated with one or more lumiphoric materials. As shown, twelve solid state emitter chips 185 are provided in contact with the electrical traces or metal patterns 182 arranged over a submount 181, and cathodes of the solid state emitter chips 185 are connected by the wirebonds 186 to the electrical traces or metal patterns 182. In certain embodiments, the optical element 189 may include one or more functional materials, such as lumiphoric material, notch filtering material, and/or scattering material, which may be doped, coated, or otherwise provided in or on the optical element 189. The solid state emitter chips 185 may be selected from various light color bins to provide a combined light output with appropriate color characteristics for a desired application. The unfiltered efficiency of the solid state emitter package 180 with a warm white color may be on the order of 100 lumens per watt (lm/W), prior to any filtering from the optical element 189; however, if the solid state emitter package 180 is binned for a cool white color, then an efficiency on the order of about 150 lm/W can be achieved (i.e., prior to any filtering).

Embodiments disclosed herein may be suited for various types of lighting fixtures where melatonin suppression characteristics (i.e., low melatonin suppression conditions) that ameliorate or reduce symptoms of circadian rhythm disorders are desired. The various types of lighting fixtures include both indoor and outdoor lighting fixtures. An indoor lighting fixture with melatonin suppression characteristics described herein may be useful in various applications, such as night time lighting for hospital rooms where circadian rhythms of patients may not be disrupted while maintaining good visibility for doctors and nurses. Other indoor applications may include night time lighting for nurseries and other household bedrooms as well as agriculture and livestock applications. An indoor lighting device may include at least one of an area light, a downlight, a high-bay or low-bay lighting fixture, a suspended lighting fixture, a troffer, a wall-mounted or ceiling mounted fixture, track lighting, a table or floor lamp, and a light bulb. An outdoor lighting fixture with melatonin suppression characteristics described herein may be useful in various applications, including at least one of an area light, a street or roadway light fixture, a canopy light fixture, a soffit light fixture, a parking garage lighting fixture, flood lighting, and a wall-mounted or ceiling mounted outdoor fixture. In that regard, circadian rhythms may not be disrupted and light pollution may be reduced.

Figure 16A:
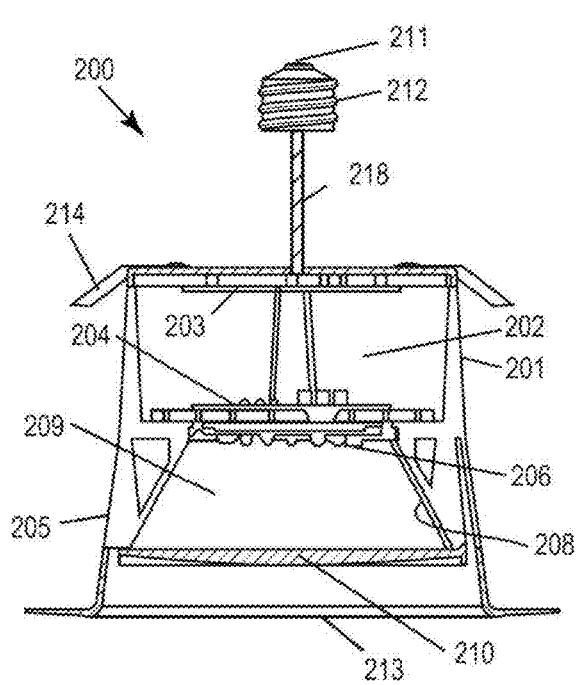
FIG. 16A is a cross-sectional view of a lighting device according to one embodiment of the disclosure embodied in a substantially cylindrical downlight intended for in-ceiling mounting and including multiple LEDs.
Figure 16B:
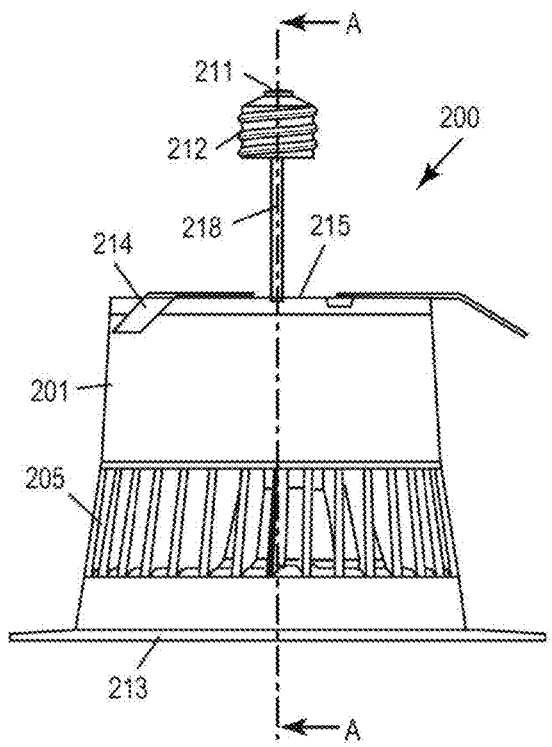
FIG. 16B is a side elevation view of the lighting device of FIG. 16A.
Figure 16C:
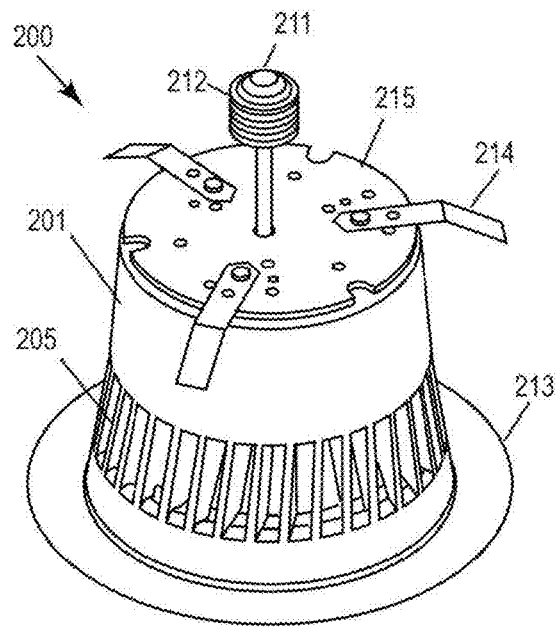
FIG. 16C is an upper perspective view of the lighting device of FIGS. 16A-16B.
Figure 16D:
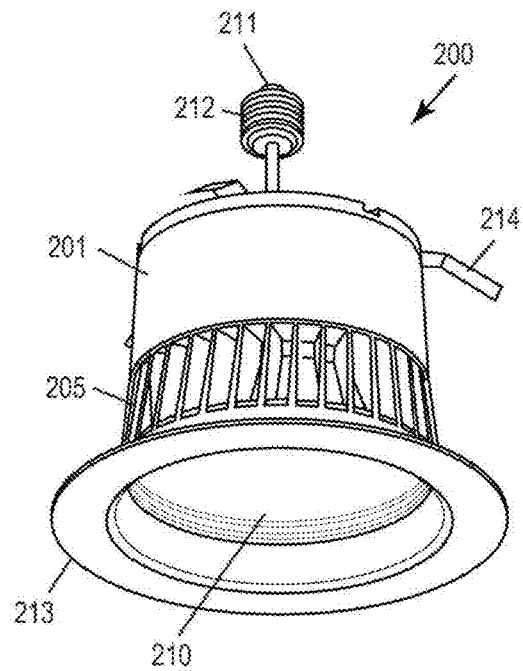
FIG. 16D is a lower perspective view of the lighting device of FIGS. 16A-16C.

FIGS. 16A-16D illustrate a lighting device according to one embodiment of the disclosure, embodied in a substantially cylindrical downlight 200 intended for in-ceiling mounting and including multiple LEDs as part of a LED module 206. FIG. 16A is a cross-sectional view of the downlight 200 taken along the line A-A in FIG. 16B. The downlight 200 includes a generally cylindrical base housing 201 and a heatsink housing 205 that in combination form a body structure. Mounting elements 214 such as rotatable spring tabs are arranged along an upper surface 215 of the base housing 201. A cable 218 extends between the base housing 201 and an Edison (screw-type) male connector forming a threaded lateral contact 212 and a foot contact 211. The base housing 201 defines an interior volume 202 containing printed circuit boards 203, 204 that include operative elements such a power converter, a controller module (e.g., including at least one processor and a memory), one or more transceivers (e.g., wireless transceivers), LED driver modules, sensor modules, detectors, voice recognition circuitry, and the like. The heatsink housing 205 defines an inner cavity 209 that includes a reflective surface 208 and is further bounded by a light transmissive optical element such as a lens and/or a diffuser 210. A trim bezel 213 is arranged proximate to an open end of the heatsink housing 205. The downlight 200 may include any suitable features disclosed herein, and is preferably arranged to execute any one or more functions and/or method steps described herein.

Figure 17A:
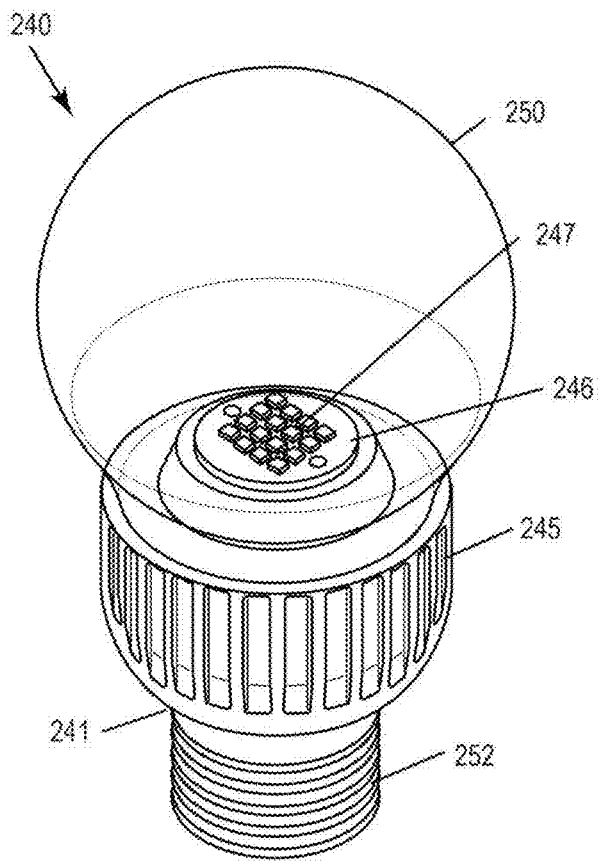
FIG. 17A is an upper perspective view of a light bulb including multiple LEDs arranged in a two-dimensional array according to one embodiment of the disclosure.
Figure 17B:
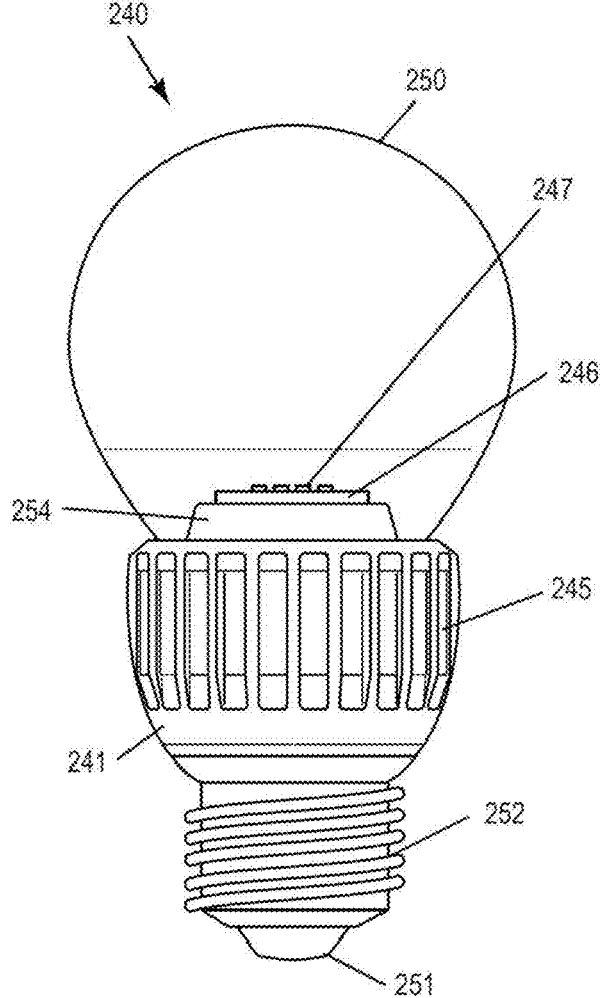
FIG. 17B is a side elevation view of the light bulb of FIG. 17A.

FIGS. 17A-17B illustrate a light bulb 240 including multiple LEDs 247 arranged in a two-dimensional array within a cavity bounded by a light transmissive globe or lens 250 according to one embodiment of the disclosure. Each LED 247 may have associated therewith multiple lumiphoric materials. The LEDs 247 are arranged on a single substantially planar emitter support surface 246, which may or may not be elevated by a pedestal 254. In other embodiments, the LEDs 247 may be arranged in strips within an interior volume of the lens 250 to emulate the appearance of an incandescent filament. The light bulb 240 includes a body structure 241 having an associated external heatsink 245. An Edison (screw-type) connector including a threaded lateral contact 252 and a foot contact 251 extend from one end of the body structure 241 opposing the lens 250. The body structure 241 defines an interior volume containing at least one printed circuit board (not shown) that includes operative elements such as a power converter, a controller module (e.g., including at least one processor and a memory), one or more transceivers (e.g., wireless transceivers), LED driver modules, sensor modules, detectors, voice recognition circuitry, and the like. The light bulb 240 may include any suitable features disclosed herein.

Figure 18A:
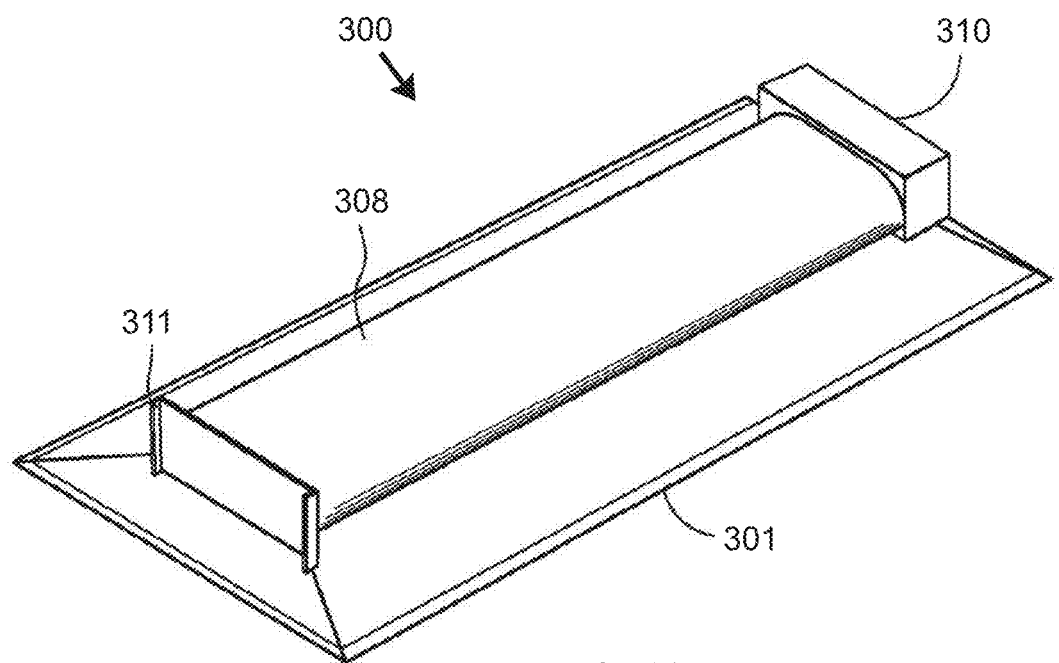
FIG. 18A is an upper perspective view of a troffer-type light fixture arranged to incorporate multiple solid state emitters as disclosed herein.
Figure 18B:
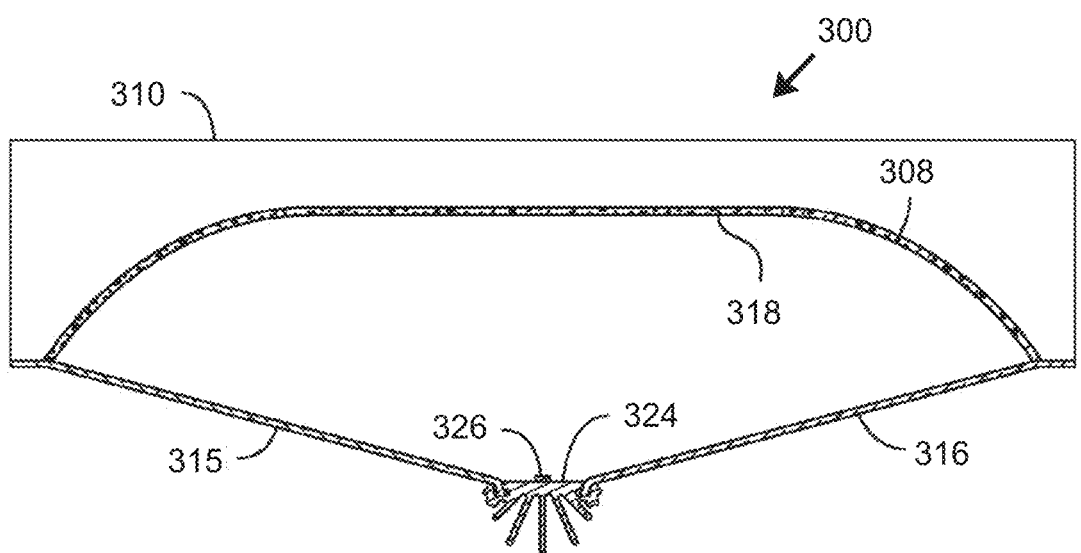
FIG. 18B is a side cross-sectional view of a portion of the light fixture of FIG. 18A.

FIGS. 18A-18B illustrate a troffer-type (in-ceiling linear) light fixture 300 arranged to incorporate multiple solid state emitters (e.g., LEDs) 326 as disclosed herein. In certain embodiments, one or more lumiphoric materials may be associated with one or more solid state emitters 326. Optionally, the light fixture 300 may include one or more notch filtering materials, such as may be associated with the solid state emitters 326, which may be applied to or included in a linear reflector (e.g., by doping, impregnation, coating, etc.), or may be applied to or integrated with one or more light transmissive lens plates 315, 316 to cause the light emitted from the light fixture 300 to exhibit a spectral notch. The light fixture 300 includes a pan 301, a heatsink 302, a reflector 308, and end caps 310, 311. The end cap 310 is larger than the end cap 311 and is shaped to act as a circuit box to house electronics (e.g., rectifiers, regulators, timing circuitry, etc.) used to drive and control the light source. The reflector 308 may include a diffusively reflective or specularly reflective surface 318. Although a reflector may take various shapes, in the illustrated embodiment, the reflector 308 includes a flat region 324 opposite the heatsink 302. In alternative embodiments, the reflector 308 could be parabolic in shape, or include two or more parabolic regions. The light fixture 300 also includes a diffuser lens assembly including the lens plates 315, 316, disposed adjacent to sides of the heatsink 302. As illustrated, the one or more solid state emitters 326 are arranged facing the reflector 308 in a manner such that a majority of LED emissions interact with the reflector 308 before exiting the light fixture 300 via the lens plates 315, 316. In alternative embodiments, the one or more solid state emitters 326 are arranged facing the lens plates 315, 316 such that a smaller portion of LED emissions interact with the reflector 308 before exiting the light fixture 300. In such embodiments, the lens plates 315, 316 may be replaced with a single continuous lens plate that covers the reflector 308.

Figure 19A:
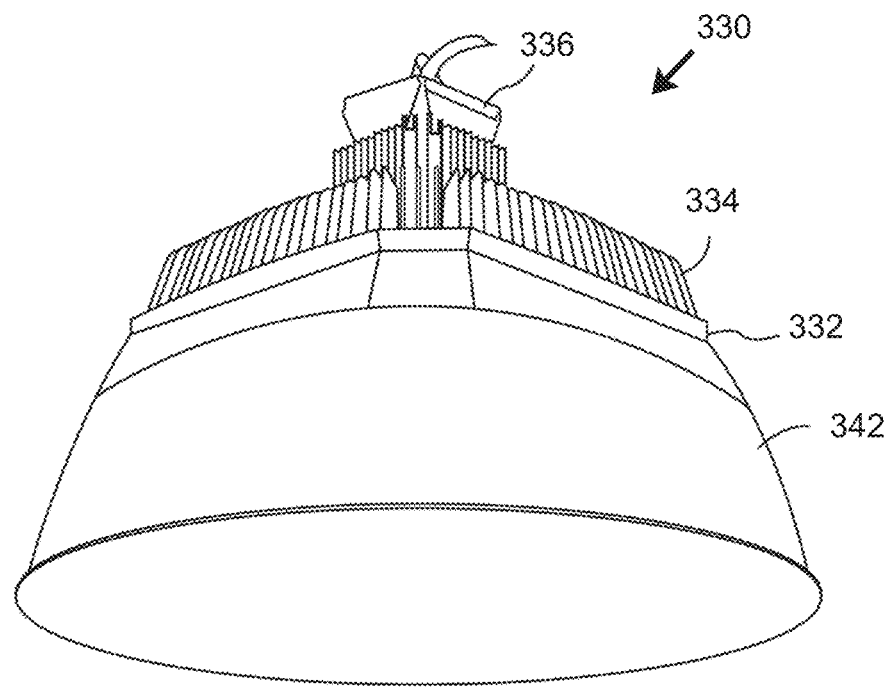
FIGS. 19A and 19B illustrate a high bay/low bay solid state lighting fixture including multiple solid state light emitters.
Figure 19B:
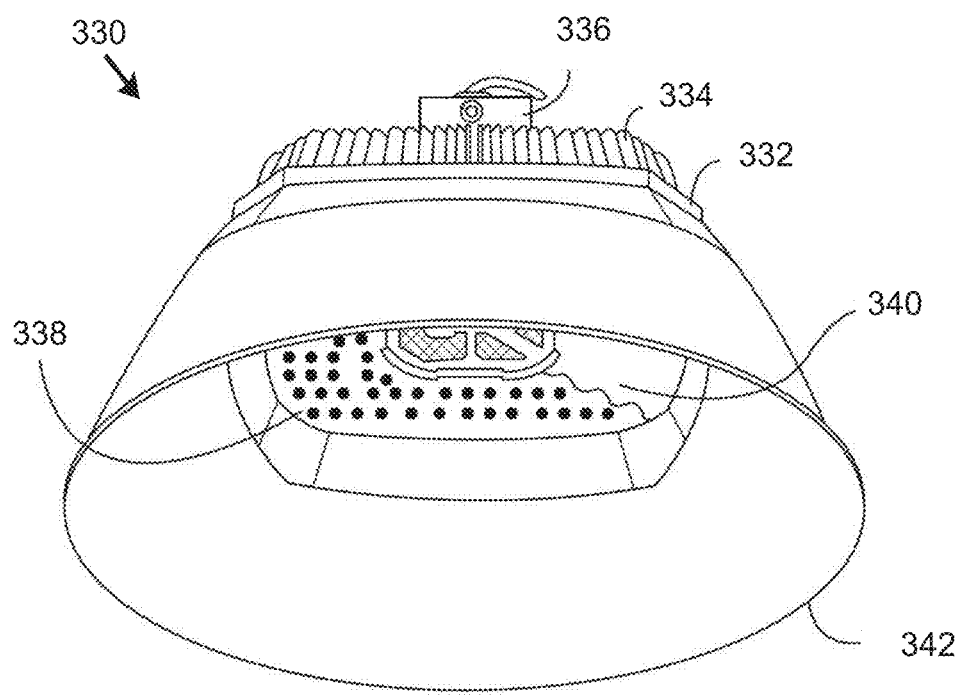

FIGS. 19A-19B illustrate a high bay/low bay type solid state lighting fixture 330 including a frame 332 over which a heatsink 334 and an electronics housing 336 are mounted. An LED array 338 is mounted on a bottom side of the frame 332 and may be covered by a lens 340. As illustrated, a portion of the lens 340 is shown as being removed to expose the LED array 338. A reflector 342 may be provided around the LED array 338 to aid in directing and mixing light emitted from the LED array 338 for general illumination.

Figure 20A:
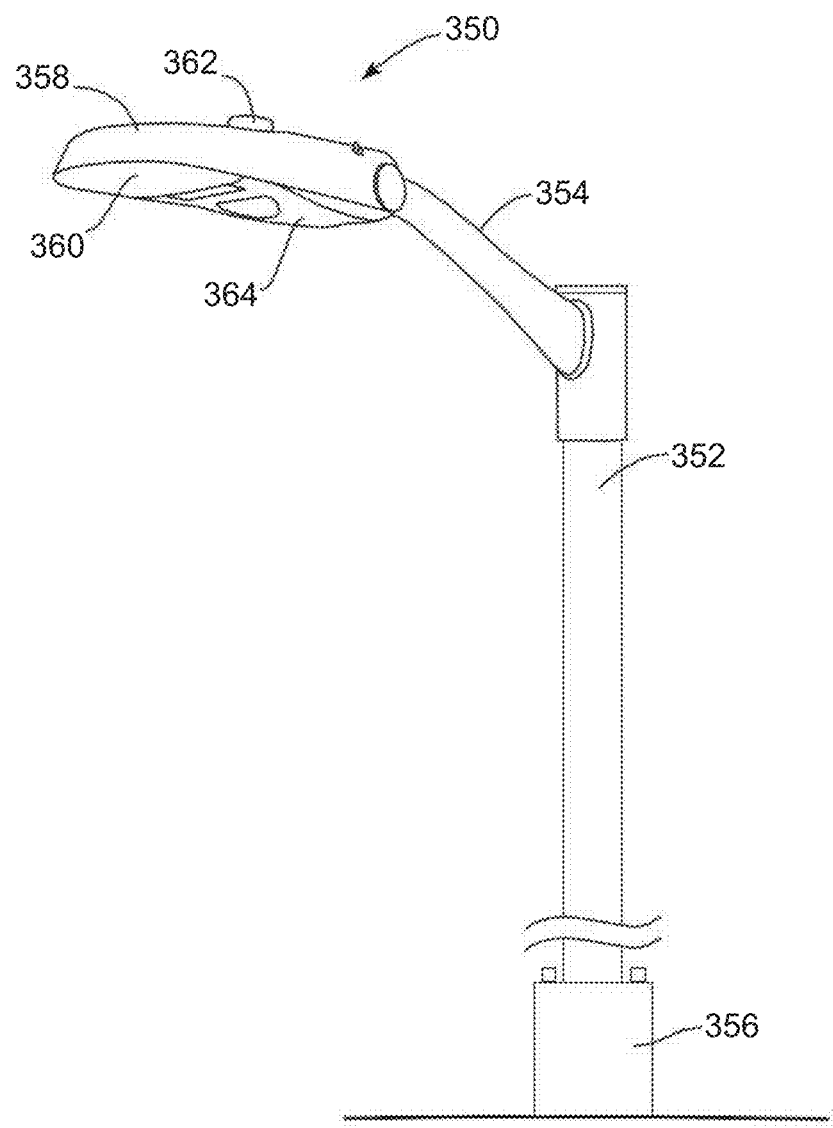
FIG. 20A illustrates an outdoor lighting fixture mounted to a utility pole according to some embodiments of the disclosure.

FIGS. 20A-20E illustrate a first outdoor floodlight (e.g., street or roadway lamp) lighting fixture 350 that may include solid state light emitters and lumiphoric materials according to embodiments described herein. With reference to FIG. 20A, the lighting fixture 350 is mounted to a utility pole 352 by a tenon 354. The tenon 354 in this example extends outward from a top portion of the utility pole 352, and the lighting fixture 350 is attached to the free end of the tenon 354. The bottom of the utility pole 352 may be mounted to a pole base 356, which is securely mounted in or on the ground or other surface. As provided herein, the tenon 354 is defined as the mounting structure to which the lighting fixture 350 is directly mounted. The tenon 354 may be an integral extension or part of the utility pole 352, attached to the utility pole 352, or attached directly to a structure other than a pole, such as a building, wall, frame, sign, and the like.

Typically, the lighting fixture 350 has a housing 358 in which a light source 360 and an ambient light sensor 362 are mounted. In normal operation, the ambient light sensor 362 provides information bearing on ambient light levels, and based on these ambient light levels, the light source 360 will turn on and off. When ambient light levels fall below a certain level, the light source 360 will turn on, and when ambient light levels rise above a certain level, the light source 360 will turn off in traditional fashion. While the light source 360 may take various configurations, the one illustrated incorporates LEDs and sufficient control circuitry to drive the LEDs as desired in response to information provided by the ambient light sensor 362 as well as any other sensors, such as occupancy, motion, sound, vibration, temperature, and like sensors, as well as a wired or wireless controllers. As described further below, an access cover 364 provides access to the interior of the housing 358. Such access may facilitate connecting the light source power as well as securely attaching the lighting fixture 350 to the tenon 354. In some embodiments, the access cover 364 is hinged at the rear of the housing 358 and rotates downward to provide access to the interior of the housing 358. The access cover 364 may use various mechanisms to lock into a closed position. These mechanisms may range from fasteners, such as screws and bolts, to snap-fit and magnetic configurations.

The housing 358 and the access cover 364 may be formed using an over-molding process that employs various mold compounds, such as thermoset bulk molding compounds, fiber reinforced thermoplastics, or un-filled thermoplastics. These mold compounds may be polymer based, but are not limited thereto, and may include various types of fibers, such as glass fibers, for reinforcement. With an over-mold process, the housing 358 and the various features thereof may be integrally formed as a single structure. Further, various features that are provided on or within the housing 358 may be affixed to, surrounded by, or otherwise formed within the structure. The tenon 354 may be formed from the same or different materials as the housing 358. In various embodiments, the tenon 354 may be formed from metals, such as, aluminum and steel, as well as from composite materials, such as carbon reinforced polymers and the like.

Figure 20B:
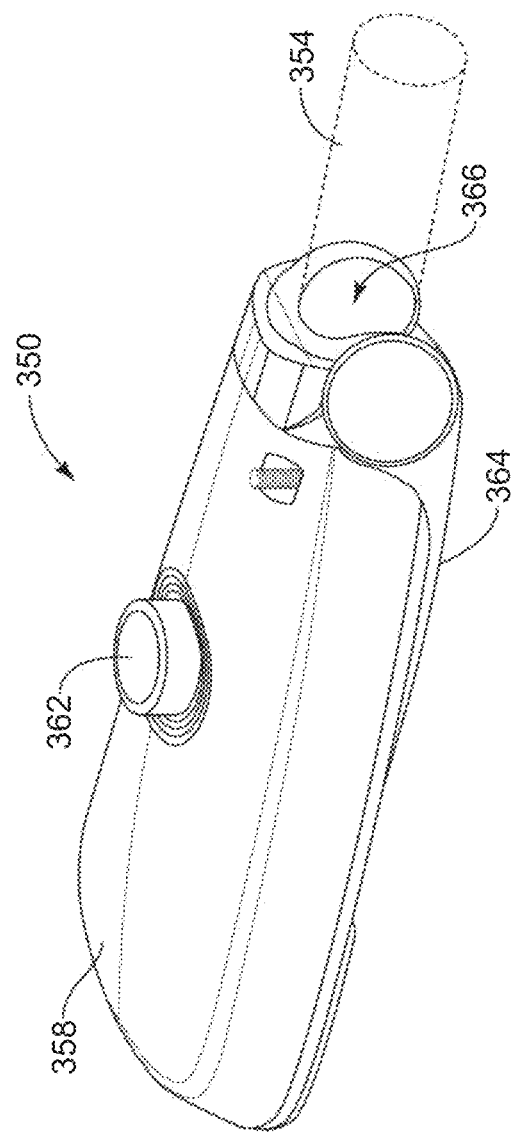
FIG. 20B illustrates a top-rear isometric view of the lighting fixture of FIG. 20A.
Figure 20C:
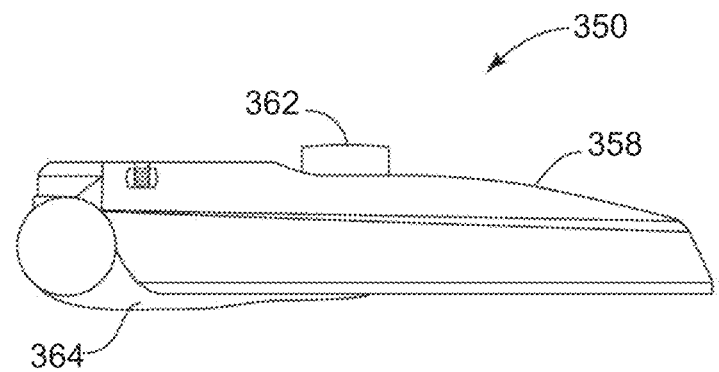
FIG. 20C is a side plan view of the lighting fixture of FIG. 20A.
Figure 20D:
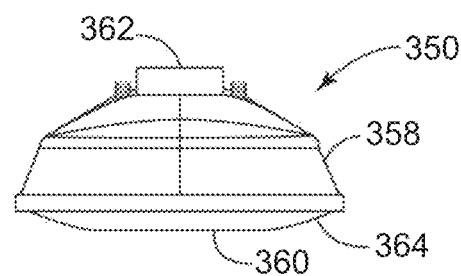
FIG. 20D is a front plan view of the lighting fixture of FIG. 20A.
Figure 20E:
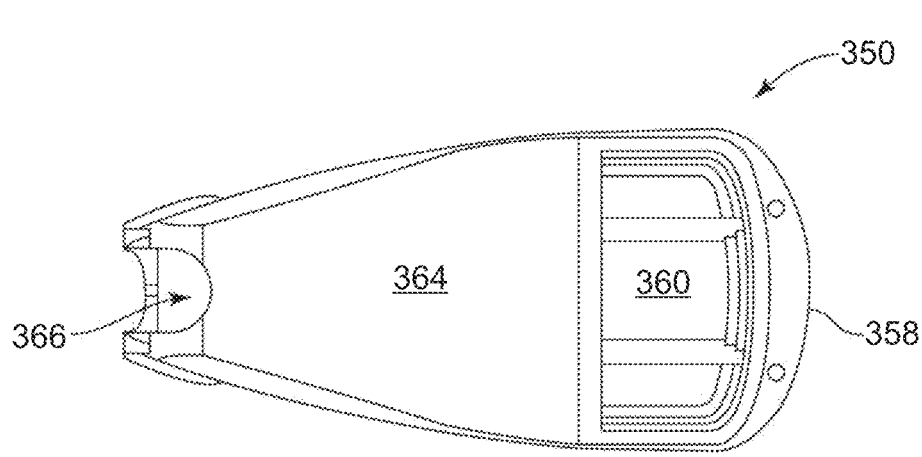
FIG. 20E is a bottom plan view of the lighting fixture of FIG. 20A.

FIG. 20B provides a rear isometric view of the lighting fixture 350, including a view of the housing 358 and the ambient light sensor 362 that is on an opposite side of the lighting fixture 350 from the access cover 364. An opening at the rear of the lighting fixture 350 is referred to as a tenon cradle 366. The tenon cradle 366 receives the tenon 354, and an attachment mechanism, which will be described further below, is used to securely attach the lighting fixture 350 to the tenon 354. FIGS. 20C, 20D, and 20E, provide side, front, and bottom views, respectively, of the lighting fixture 350 including the housing 358, the light source 360, the ambient light sensor 362, the access cover 364, and the tenon cradle 366. As previously described, the light source 360 includes LEDs and sufficient control circuitry to drive the LEDs. The light source 360 may further include one or more lenses or reflectors configured to direct light in a desired emission pattern. In some embodiments, the light source 360 includes a waveguide, or a waveguide optic, configured to receive light from the LEDs and direct it in a desired emission pattern.

Figure 21A:
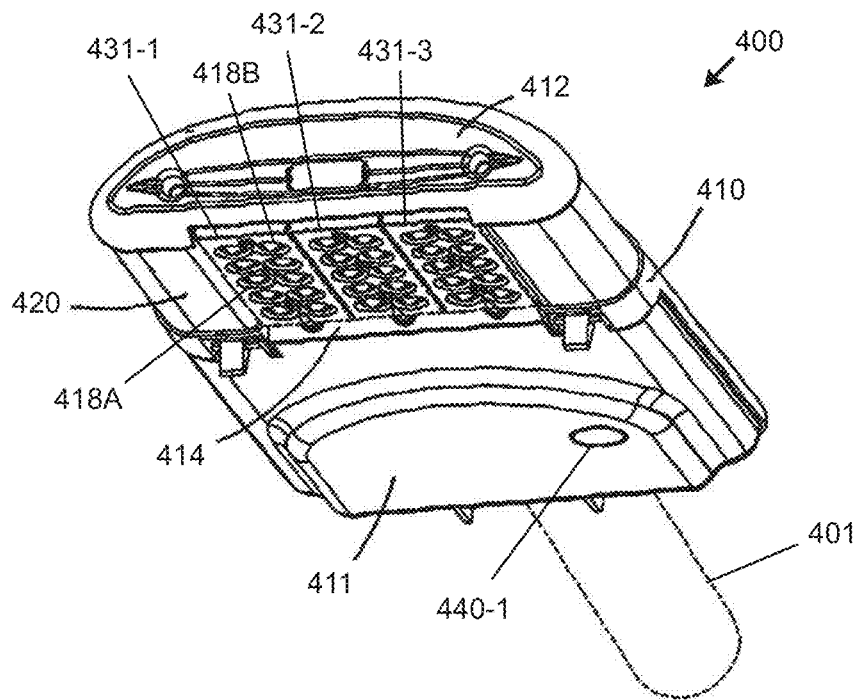
FIGS. 21A-21B illustrate an outdoor lighting fixture according to some embodiments of the disclosure.
Figure 21B:
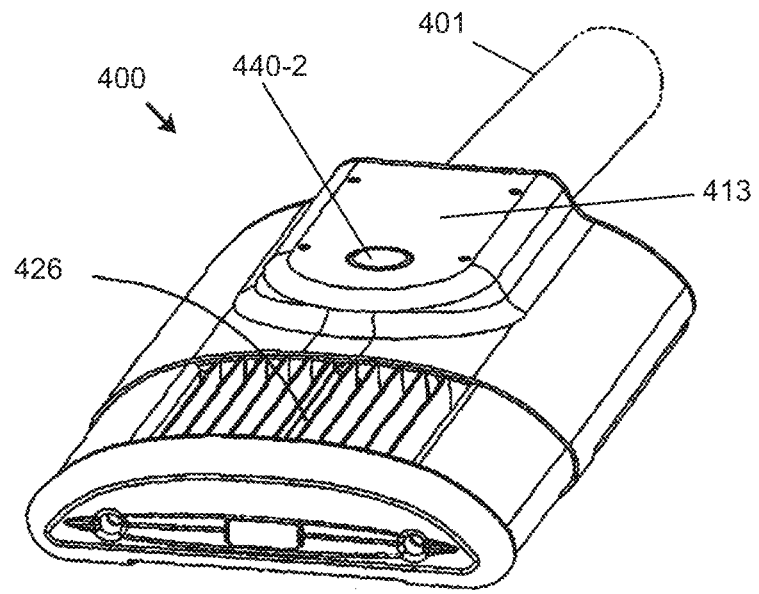

FIGS. 21A-21B illustrate a second outdoor floodlight (e.g., street or roadway lamp) lighting fixture 400 that may include solid state light emitters and lumiphoric materials as described herein. The lighting fixture 400 includes a housing 410 including a base portion 411 supported by an elongated pole 401 or other support. Multiple LEDs modules 431-1, 431-2, 431-3 each including multiple LEDs 418A, 418B arranged in an array are provided along a lower surface 420 of the lighting fixture 400 between the pole 401 and an end cap 412. The LED modules 431-1, 431-2, 431-3 are arranged proximate to an air gap 414 permitting heat to be dissipated to a heat spreader or heat sink 426 (arranged along an upper surface 413 of the housing 410) and transferred to an ambient environment. The lighting fixture 400 may include at least one receiver or sensor element 440-1, 440-2, which may embody any one or more of a GPS receiver, a radio frequency receiver, an ambient light sensor, an image sensor, a temperature sensor, a motion sensor, a sound sensor, a timer, or the like.

Figure 22A:
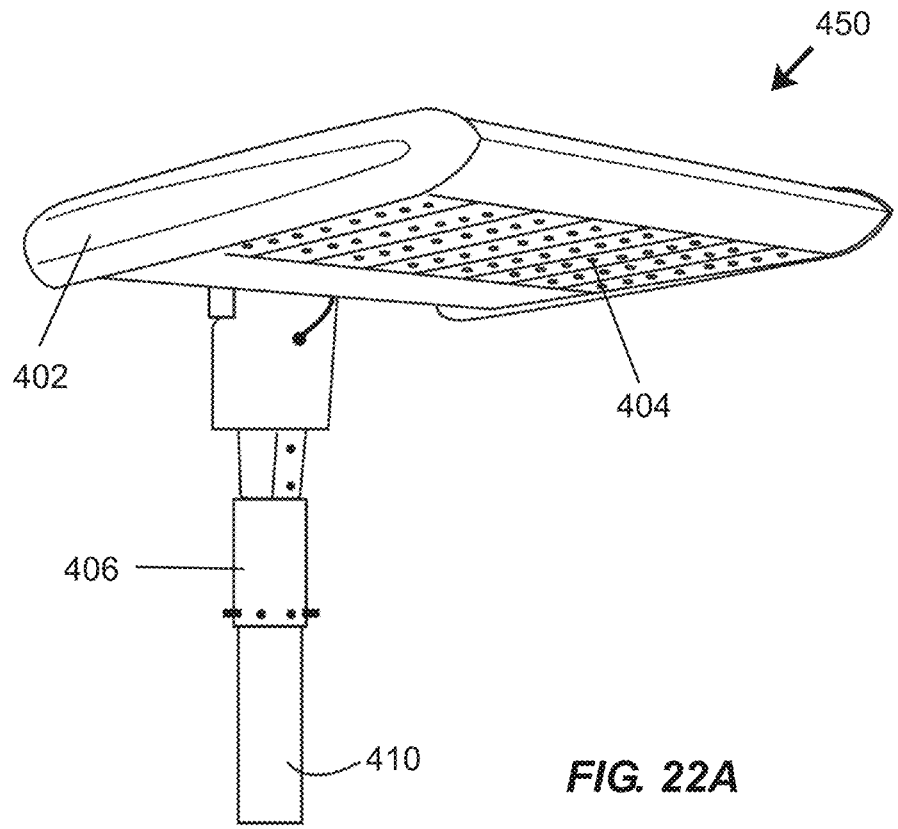
FIGS. 22A-22B illustrate an outdoor lighting fixture according to some embodiments of the disclosure.
Figure 22B:
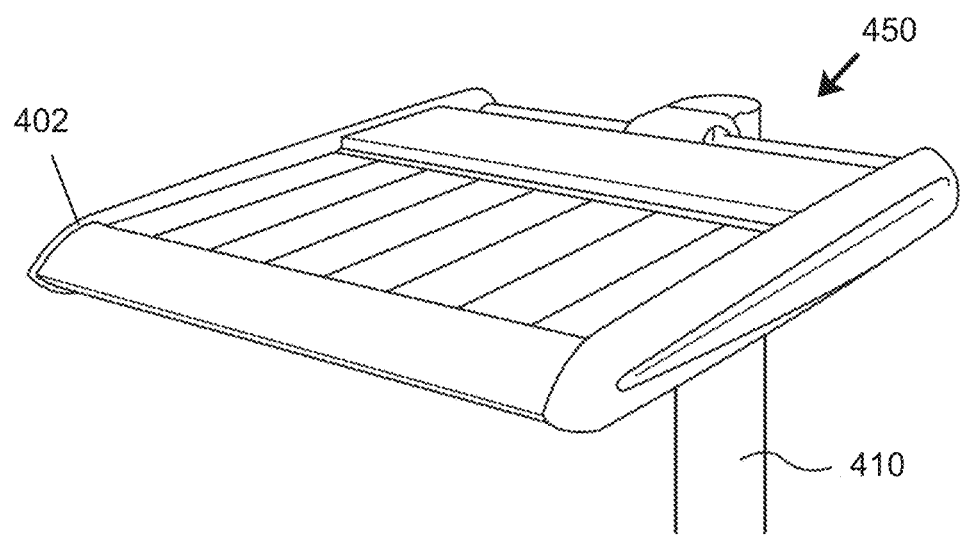

FIGS. 22A-22B illustrate a third outdoor floodlight (e.g., street or roadway lamp) lighting fixture 450 including a body structure 402 housing an array of solid state light emitters 404 as disclosed herein. An interface structure 406 may be used to couple the lighting fixture 450 to a pole 410. Outdoor light fixtures such as shown in FIGS. 27A-27B may be mounted to poles, tenons, or the like. The array of solid state light emitters 404 may be used to illuminate a desired environment, such as a roadway, a parking lot, a street, or the like.

Any of the lighting fixtures described in FIGS. 16A-16D, 17A-17B, 18A-18B, 19A-19B, 20A-20E, 21A-21B, and 22A-22B may be configured to provide aggregated emissions having a CCT in a range of from about 1800 K to about 2600 K. In further embodiments, the aggregated emissions have a CCT in a range of from about 1800 K to about 2300 K, or in a range of from about 2150 K to 2250 K. In some embodiments, the aggregated emissions have a Duv in a range from 0.005 to 0.020; in further embodiments, the aggregated emissions have a Duv in a range from 0.005 to 0.015; and in still further embodiments, the aggregated emissions have a Duv in a range from 0.005 to 0.010. In some embodiments, the aggregated emissions have a CRI of at least 65. In further embodiments, the aggregated emissions have a CRI of at least 70. In further embodiments, the aggregated emissions have a CRI in a range of 65 to 85, or in a range of 65 to 80, or in a range of 70 to 90, or in a range of 70 to 80.

In some embodiments, any of the lighting fixtures described in FIGS. 16A-16D, 17A-17B, 18A-18B, 19A-19B, 20A-20E, 21A-21B, and 22A-22B have multiple LEDs, each of which is configured to provide the same aggregated emissions as previously described. In other embodiments, different LEDs of the multiple LEDs have different emission characteristics that collectively form the aggregated emissions of a particular lighting fixture. For example, a solid state lighting device may include a first electrically activated solid state emitter configured to generate emissions having a peak wavelength in a range from 430 nm to 480 nm, a first lumiphoric material arranged to receive at least a portion of the emissions of the first electrically activated solid state emitter and responsively generate first lumiphor emissions having a peak wavelength in a range from 540 nm to 570 nm, a second electrically activated solid state emitter configured to generate emissions having a peak wavelength in a range from 430 nm to 480 nm, and a second lumiphoric material arranged to receive at least a portion of the emissions of the second electrically activated solid state emitter and responsively generate second lumiphor emissions having a peak wavelength in a range from 605 nm to 650 nm. Aggregated emissions of the solid state lighting device thereby include a portion of emissions of the first and second electrically activated solid state emitters, the first lumiphor emissions, and the second lumiphor emissions.

Embodiments as disclosed herein may provide one or more of the following beneficial technical effects: reducing circadian rhythm disruptions of illumination provided by lighting devices while maintaining desirable color rendering characteristics; reducing light pollution in the night sky; and reducing energy consumption required for light fixtures.

Those skilled in the art will recognize improvements and modifications to the preferred embodiments of the present disclosure. All such improvements and modifications are considered within the scope of the concepts disclosed herein and the claims that follow.

What is claimed is:

1. A solid state lighting device comprising:
   at least one electrically activated solid state emitter configured to generate emissions having a peak wavelength in a range of 430 nanometers (nm) to 480 nm;
   a first lumiphoric material arranged to receive at least a portion of the emissions of the at least one electrically activated solid state emitter and responsively generate first lumiphor emissions having a peak wavelength in a range of 540 nm to 570 nm; and
   a second lumiphoric material arranged to receive at least a portion of the emissions of the at least one electrically activated solid state emitter and responsively generate second lumiphor emissions having a peak wavelength in a range of 605 nm to 650 nm;
   wherein aggregated emissions of the solid state lighting device include at least a portion of the emissions of each of the at least one electrically activated solid state emitter, the first lumiphor emissions, and the second lumiphor emissions; and
   wherein the aggregated emissions have a correlated color temperature (CCT) in a range of 1800 Kelvin (K) to 2600 K, and have a Duv of at least 0.005.

2. The solid state lighting device of claim 1 wherein the aggregated emissions have a CCT in a range of 1800 K to 2300 K.

3. The solid state lighting device of claim 1 wherein the aggregated emissions have a CCT in a range of 2150 K to 2250 K.

4. The solid state lighting device of claim 1 wherein the aggregated emissions have a Duv in a range of 0.005 to 0.020.

5. The solid state lighting device of claim 1 wherein the aggregated emissions have a color rendering index (CRI) of at least 65.

6. The solid state lighting device of claim 5 wherein the aggregated emissions have a CRI in a range of 65 to 85.

7. The solid state lighting device of claim 1 wherein the first lumiphoric material and the second lumiphoric material are dispersed together in a common binder.

8. The solid state lighting device of claim 1 wherein the first lumiphoric material and the second lumiphoric material are arranged in discrete layers on the at least one electrically activated solid state emitter.

9. The solid state lighting device of claim 8 wherein the second lumiphoric material is arranged between the first lumiphoric material and the at least one electrically activated solid state emitter.

10. The solid state lighting device of claim 1 wherein the solid state lighting device comprises a light-emitting diode (LED) package.

11. The solid state lighting device of claim 1 wherein the solid state lighting device comprises an outdoor lighting fixture.

12. The solid state lighting device of claim 1 wherein the solid state lighting device comprises an indoor lighting fixture.

13. A solid state lighting device comprising:
    a first electrically activated solid state emitter configured to generate emissions having a peak wavelength in a range of 430 nanometers (nm) to 480 nm;
    a first lumiphoric material arranged to receive at least a portion of emissions of the first electrically activated solid state emitter and responsively generate first lumiphor emissions;
    a second electrically activated solid state emitter; and
    a second lumiphoric material arranged to receive at least a portion of emissions of the second electrically activated solid state emitter and responsively generate second lumiphor emissions, wherein the second lumiphor emissions have a peak wavelength that differs from a peak wavelength of the first lumiphor emissions by at least 25 nm;
    wherein aggregated emissions of the solid state lighting device include at least a portion of the emissions of each of the first electrically activated solid state emitter, the second electrically activated solid state emitter, the first lumiphor emissions, and the second lumiphor emissions; and wherein the aggregated emissions have a correlated color temperature (CCT) in a range of 1800 Kelvin (K) to 2600 K, and have a Duv of at least 0.005.

14. The solid state lighting device of claim 13 wherein the first lumiphor emissions have a peak wavelength in a range of 540 nm to 570 nm.

15. The solid state lighting device of claim 13 wherein the second electrically activated solid state emitter is configured to generate emissions having a peak wavelength in a range of 430 nm to 480 nm and the second lumiphor emissions have a peak wavelength in a range of 605 nm to 650 nm.

16. The solid state lighting device of claim 13 wherein the aggregated emissions have a color rendering index (CRI) of at least 65.

17. The solid state lighting device of claim 16 wherein the aggregated emissions have a CRI in a range of 65 to 85.

18. A solid state lighting device comprising:
a first electrically activated solid state emitter configured to generate emissions having a peak wavelength in a range of 430 nanometers (nm) to 480 nm;
a first lumiphoric material arranged to receive at least a portion of the emissions of the first electrically activated solid state emitter and responsively generate first lumiphor emissions having a peak wavelength in a range of 540 nm to 570 nm; and
a second electrically activated solid state emitter configured to generate emissions having a peak wavelength in a range of 605 nm to 650 nm;
wherein aggregated emissions of the solid state lighting device include at least a portion of the emissions of each of the first electrically activated solid state emitter, the first lumiphor emissions, and the second electrically activated solid state emitter; and
wherein the aggregated emissions have a correlated color temperature (CCT) in a range of 1800 Kelvin (K) to 2600 K, and have a Duv of at least 0.005.

19. The solid state lighting device of claim 18 further comprising a second lumiphoric material arranged to receive at least a portion of the emissions of the first electrically activated solid state emitter and responsively generate second lumiphor emissions having a peak wavelength in a range of 605 nm to 650 nm.

20. The solid state lighting device of claim 18 wherein the aggregated emissions have a color rendering index (CRI) of at least 65.

21. The solid state lighting device of claim 20 wherein the aggregated emissions have a CRI in a range of 65 to 85.

22. A solid state lighting device comprising:
a first electrically activated solid state emitter;
a first lumiphoric material arranged to receive at least a portion of emissions of the first electrically activated solid state emitter and responsively generate first lumiphor emissions; and
at least one other light emitter including at least one of the following items (a) or (b): (a) a second electrically activated solid state emitter, or (b) a second lumiphoric material arranged to receive at least a portion of emissions of the first electrically activated solid state emitter and responsively generate second lumiphor emissions;
wherein aggregated emissions of the solid state lighting device include at least a portion of the emissions of each of the first electrically activated solid state emitter, the first lumiphoric material, and the at least one other light emitter; and
wherein the aggregated emissions have a circadian stimulus (CS) value of less than 0.17, and have a Duv of at least 0.005.

23. The solid state lighting device of claim 22 wherein the aggregated emissions comprises at least one of the following features (i), (ii), or (iii):
(i) a correlated color temperature (CCT) in a range of 1950 K to 2050 K, a color rendering index (CRI) of at least 70, and a CS value of less than 0.125; or
(ii) a CCT in a range of 2200 K to 2300 K, a CRI of at least 70, and a CS value of less than 0.145; or
(iii) a CCT in a range of 2450 K to 2550 K, a CRI of at least 70, and a CS value of less than 0.17.

* * * * *